United States Patent
Masaki et al.

(10) Patent No.: US 10,841,682 B2
(45) Date of Patent: Nov. 17, 2020

(54) COMMUNICATION NETWORK OF IN-EAR UTILITY DEVICES HAVING SENSORS

(71) Applicant: SmartEar, Inc., San Francisco, CA (US)

(72) Inventors: Kinuko Masaki, San Francisco, CA (US); Dean Gardner, San Francisco, CA (US); Victor Valenzuela, Hayward, CA (US)

(73) Assignee: SmartEar, Inc., San Francisco, CA (US)

( * ) Notice: Subject to any disclaimer, the term of this patent is extended or adjusted under 35 U.S.C. 154(b) by 0 days.

(21) Appl. No.: 16/779,588

(22) Filed: Feb. 1, 2020

(65) Prior Publication Data

US 2020/0177982 A1    Jun. 4, 2020

Related U.S. Application Data

(63) Continuation of application No. 15/163,891, filed on May 25, 2016, now abandoned.

(51) Int. Cl.
*H04R 25/00* (2006.01)
*H04R 1/10* (2006.01)
(Continued)

(52) U.S. Cl.
CPC ....... *H04R 1/1016* (2013.01); *A61B 5/02028* (2013.01); *A61B 5/02055* (2013.01);
(Continued)

(58) Field of Classification Search
CPC ............ A61B 5/02028; A61B 5/02055; A61B 5/0404; A61B 5/0476; A61B 5/1118; A61B 5/6817; A61B 2560/0252; A61B 5/02405; A61B 5/02438; A61B 5/0533; A61B 5/0816; A61B 5/0833; A61B 5/11; A61B 5/14552; A61B 2562/0219; A61B 2562/0223; A61B 2562/0247; A61B 2562/029; A61B 5/02; A61B 5/6815; H04R 1/1091; H04R 2201/103; H04R 2201/403; H04R 2410/05; H04R 2420/07;
(Continued)

(56) References Cited

U.S. PATENT DOCUMENTS 1,852,130 A    4/1932  Schier
1,893,143 A    1/1933  Henry
(Continued)

FOREIGN PATENT DOCUMENTS

WO    WO2014/138735 A1    9/2014

OTHER PUBLICATIONS

"Snoring and Sleep Apnea, Sleep Well—Feel Better," 4th Ed. (2008), Dr. Ralph A. Pascualy, M.D., cover, descriptive pages, and p. 34 (4 pages).
(Continued)

*Primary Examiner* — Phylesha Dabney
(74) *Attorney, Agent, or Firm* — AWA Sweden AB; Thomas L. Ewing

(57) ABSTRACT

An embodiment of the invention provides a wireless in-ear utility device that rests in the user's ear canal near the user's eardrum. The in-ear utility device may be configured in a variety of ways, including, but in no way limited to a smart in-ear utility device, a flexible personal sound amplification product, a personal music player, a "walkie-talkie" and the like.

20 Claims, 15 Drawing Sheets

(51) Int. Cl.

| | | |
|---|---|---|
| *H04R 29/00* | (2006.01) | |
| *A61B 5/0205* | (2006.01) | |
| *A61B 5/02* | (2006.01) | |
| *A61B 5/0404* | (2006.01) | |
| *A61B 5/0476* | (2006.01) | |
| *A61B 5/00* | (2006.01) | |
| *A61B 5/021* | (2006.01) | |
| *A61B 5/024* | (2006.01) | |
| *A61B 5/053* | (2006.01) | |
| *A61B 5/08* | (2006.01) | |
| *A61B 5/083* | (2006.01) | |
| *A61B 5/11* | (2006.01) | |
| *A61B 5/1455* | (2006.01) | |
| *H04R 3/00* | (2006.01) | |
| *H04R 25/02* | (2006.01) | |

(52) U.S. Cl.
CPC .......... *A61B 5/0404* (2013.01); *A61B 5/0476* (2013.01); *A61B 5/6817* (2013.01); *H04R 1/1041* (2013.01); *H04R 29/001* (2013.01); *A61B 5/021* (2013.01); *A61B 5/02405* (2013.01); *A61B 5/02438* (2013.01); *A61B 5/0533* (2013.01); *A61B 5/0816* (2013.01); *A61B 5/0833* (2013.01); *A61B 5/11* (2013.01); *A61B 5/1118* (2013.01); *A61B 5/14552* (2013.01); *A61B 5/6815* (2013.01); *A61B 2560/0252* (2013.01); *A61B 2562/029* (2013.01); *A61B 2562/0219* (2013.01); *A61B 2562/0223* (2013.01); *A61B 2562/0247* (2013.01); *H04R 1/1091* (2013.01); *H04R 3/005* (2013.01); *H04R 25/02* (2013.01); *H04R 25/356* (2013.01); *H04R 25/65* (2013.01); *H04R 25/652* (2013.01); *H04R 25/656* (2013.01); *H04R 2201/103* (2013.01); *H04R 2201/403* (2013.01); *H04R 2410/05* (2013.01); *H04R 2420/07* (2013.01); *H04R 2460/03* (2013.01)

(58) Field of Classification Search
CPC .. H04R 2460/03; H04R 25/02; H04R 25/356; H04R 25/65; H04R 25/652; H04R 25/656; H04R 3/005; H04R 1/1016; H04R 1/1041; H04R 29/001
USPC ........................................................ 381/381
See application file for complete search history.

(56) References Cited

U.S. PATENT DOCUMENTS

| | | |
|---|---|---|
| 2,248,837 A | 7/1941 | Walters |
| 2,619,960 A | 12/1952 | Reynolds |
| 2,678,973 A | 5/1954 | Newman |
| 2,754,365 A | 7/1956 | Vvalters |
| 2,971,065 A | 2/1961 | Busse |
| 2,984,726 A | 5/1961 | Roeser |
| 3,282,106 A | 11/1966 | Bowling |
| 3,815,583 A | 6/1974 | Scheidt |
| 3,983,336 A | 9/1976 | Malek |
| 4,069,400 A | 1/1978 | Johanson |
| 4,133,984 A | 1/1979 | Akiyama |
| 4,349,083 A | 9/1982 | Bennett |
| 4,359,708 A | 11/1982 | Jarosz |
| 4,539,708 A | 9/1985 | Norris |
| 4,550,227 A | 10/1985 | Topholm |
| 5,031,219 A | 7/1991 | Ward et al. |
| 5,159,936 A | 11/1992 | Yelderman |
| 5,167,235 A | 12/1992 | Seacord |
| 5,626,139 A | 5/1997 | Szeles |
| 5,654,530 A | 8/1997 | Sauer |
| 5,812,680 A | 9/1998 | Glendon |
| 6,358,281 B1 | 3/2002 | Berrang |
| 6,648,914 B2 | 11/2003 | Berrang |
| 6,920,229 B2 | 7/2005 | Boesen |
| 7,120,267 B2 | 10/2006 | Ito |
| 8,275,166 B2 | 9/2012 | Wu |
| 8,389,862 B2 | 3/2013 | Arora |
| 8,634,918 B2 | 1/2014 | Chambers |
| 8,798,298 B1 | 8/2014 | Bums |
| 8,855,345 B2 | 10/2014 | Shennib |
| 8,983,108 B2 | 3/2015 | Ho |
| 9,078,070 B2 | 7/2015 | Samuels |
| 9,456,285 B2 | 9/2016 | Bymaster |
| 9,571,913 B2 | 2/2017 | Masaki |
| 2002/0181336 A1 | 12/2002 | Shields |
| 2003/0027606 A1 | 2/2003 | Tsai |
| 2003/0195588 A1 | 10/2003 | Fischell |
| 2004/0224717 A1 | 11/2004 | Hertzberg |
| 2004/0243204 A1 | 12/2004 | Maghribi |
| 2006/0045304 A1 | 3/2006 | Lee |
| 2006/0098833 A1 | 5/2006 | Juneau |
| 2007/0154030 A1 | 7/2007 | Moses |
| 2007/0154049 A1 | 7/2007 | Levitsky |
| 2008/0063231 A1 | 3/2008 | Juneau |
| 2008/0152167 A1 | 6/2008 | Taenzer |
| 2008/0253583 A1 | 10/2008 | Goldstein |
| 2009/0010456 A1 | 1/2009 | Goldstein |
| 2009/0034775 A1 | 2/2009 | Burton |
| 2009/0052702 A1 | 2/2009 | Murphy |
| 2009/0143096 A1 | 6/2009 | Chang |
| 2009/0285437 A1 | 11/2009 | Takigawa et al. |
| 2010/0002402 A1 | 1/2010 | Rogers |
| 2010/0294285 A1 | 11/2010 | Turdjian |
| 2011/0002498 A1 | 1/2011 | Wong |
| 2011/0300806 A1 | 8/2011 | Lindahl |
| 2011/0224493 A1 | 9/2011 | Oyadiran |
| 2011/0237295 A1 | 9/2011 | Bartkowiak |
| 2011/0264447 A1 | 10/2011 | Visser |
| 2012/0114160 A1 | 5/2012 | Lin |
| 2012/0300965 A1 | 11/2012 | Samuels |
| 2013/0142363 A1 | 6/2013 | Amento |
| 2014/0112520 A1 | 4/2014 | Knudsen |
| 2014/0153761 A1 | 6/2014 | Shennib et al. |
| 2014/0153762 A1 | 6/2014 | Shennib et al. |
| 2014/0169599 A1 | 6/2014 | Solum |
| 2014/0172042 A1 | 6/2014 | Goorevich |
| 2014/0301561 A1 | 10/2014 | Silberman |
| 2014/0303452 A1 | 10/2014 | Ghaffari |
| 2015/0110313 A1 | 4/2015 | Feilner |
| 2015/0183167 A1 | 7/2015 | Molinari |
| 2015/0230022 A1 | 8/2015 | Sakai |
| 2015/0261298 A1 | 9/2015 | Li |
| 2015/0281861 A1 | 10/2015 | Karamuk |
| 2016/0049074 A1 | 2/2016 | Shennib |
| 2016/0057550 A1 | 2/2016 | Shennib |
| 2016/0162256 A1 | 6/2016 | Komaromi |
| 2016/0192050 A1 | 6/2016 | Masaki |
| 2016/0206000 A1 | 7/2016 | Lord |
| 2016/0247380 A1 | 8/2016 | Kumar |
| 2017/0262698 A1 | 9/2017 | Hoffman |

OTHER PUBLICATIONS

"Microsleep" entry from Wikipedia, http://www.wikipedia.com; entry last edited Mar. 9, 2018; entry visited Mar. 12, 2018, 9 pages.

International Search Report for PCT/US2017/034352, and International Written Opinion for PCT/US2017/034352, dated Aug. 23, 2017 and revision of same, dated Mar. 8, 2018; 16 pages.

International Search Report for PCT/US18/53249, and International Written Opinion for PCT/US18/53249, dated Nov. 20, 2018, 20 pages.

International Search Report for PCT/US15/57998, and International Written Opinion for PCT/US15/57988, dated Apr. 29, 2016, 15 pages.

"Wireless Headphones | Koss Striva Tap Wi-Fi Earbuds" by Mila Pantovich Jun. 8, 2012, JustLuxe, pp. 1-3, http://www.justluxe.com/lifestyle/electronics/feature-1780526.php (retrieved Apr. 16, 2017).

(56) References Cited

OTHER PUBLICATIONS

"Here Active Listening earbuds: Augmented reality for your ears (hands-on)" by Will Shanklin, Jan. 13, 2016, pp. 1-4, http://newatlas.com/doppler-labs-here-earbuds-hands-on/41322/ (retrieved Apr. 16, 2017).

Nap Zapper Anti-Sleep Alarm, Amazon, pp. 1-6, https://www.amazon.com/Generic-Nap-Zapper-Anti-Sleep-Alarm/dp/B000BK4KW8 (retrieved Apr. 16, 2017).

COMMUNICATION NETWORK OF IN-EAR UTILITY DEVICES HAVING SENSORS

CROSS-REFERENCE TO RELATED APPLICATIONS

The present application is a continuation of U.S. patent application Ser. No. 15/163,891 entitled "In-Ear Utility Device Having Sensors" and is related to the following applications co-filed with the '891 application identified as U.S. patent application Ser. No. 15/163,843, entitled "In-Ear Utility Device Having Tap Detector,"; U.S. patent application Ser. No. 15/163,873 entitled "In-Ear Utility Device Having Dual Microphones,"; U.S. patent application Ser. No. 15/163,908 entitled "In-Ear Utility Device Having A Humidity Sensor,"; U.S. patent application Ser. No. 15/163,931 entitled "In-Ear Utility Device Having Information Sharing,", and U.S. patent application Ser. No. 15/163,949 entitled "In-Ear Utility Device Having. Voice Recognition", which are assigned to the assignee of the present application. These applications are incorporated herein by reference in their entirety.

FIELD

Embodiments of the invention relate to systems and methods pertaining to in-ear utility devices. More particularly, an embodiment of the invention relates to systems and methods that employ in-ear electronics to provide a wireless in-ear utility device that rests in the user's ear canal.

BACKGROUND

The following description includes information that may be useful in understanding embodiments of the invention. It is not an admission that any of the information provided herein is prior art or relevant to the presently claimed invention, or that any publication specifically or implicitly referenced is prior art.

With the development of portable multimedia devices and smart phones, many types of ear pieces, such as earphones and headsets, have been developed and used. However, previous ear pieces have traditionally been bulky and uncomfortable as well as being limited in their technological abilities. Thus, the prospects for exploring new form factors for ear pieces have conventionally been limited.

Moreover, these ear pieces have conventionally been devices slaved to other devices, such as smartphones, with limited abilities to operate independently. Similarly, the prospects for exploring new and independent uses for ear pieces have also been limited conventionally.

Therefore, a need exists for more advanced in-ear utility devices that can perform an expanded set of tasks at an improved rate of performance over the devices found in the prior art.

SUMMARY OF THE INVENTION

Embodiments of the invention provide a wireless in-ear utility device, comprising a body having at least a portion shaped to fit into a user's ear canal. The body has a distal end configured to reside in the user's ear canal at a distance from 7 to 12 millimeters away from the user's ear drum. The wireless in-ear utility device includes an accelerometer located in the body, the accelerometer configured to determine changes in the user's head position. The wireless in-ear utility device also includes a data storage component having a driving safety application. The wireless in-ear utility device further includes a processor configured to execute the driving safety application, receive inputs from the accelerometer and determine if the user is falling asleep.

Embodiments of the invention include a method for operating a wireless in-ear utility device. The method comprises measuring changes to a user's head position by an accelerometer located in a body of the in-ear wireless device, wherein the body has at least a portion shaped to fit into a user's ear canal, the body having a distal end configured to reside in the user's ear canal at a distance from 7 to 12 millimeters away from the user's ear drum. The method additionally includes determining by the processor if the user is falling asleep by executing a driving safety application stored in a data storage component using the accelerometer data against instructions found in the driving safety application.

BRIEF DESCRIPTION OF THE DRAWINGS

Figures provided herein may or may not be provided to scale. The relative dimensions or proportions may vary. Embodiments of the invention may be sized to fit within an ear canal of a user.

DETAILED DESCRIPTION OF AN EMBODIMENT OF THE INVENTION

Figure 1A:
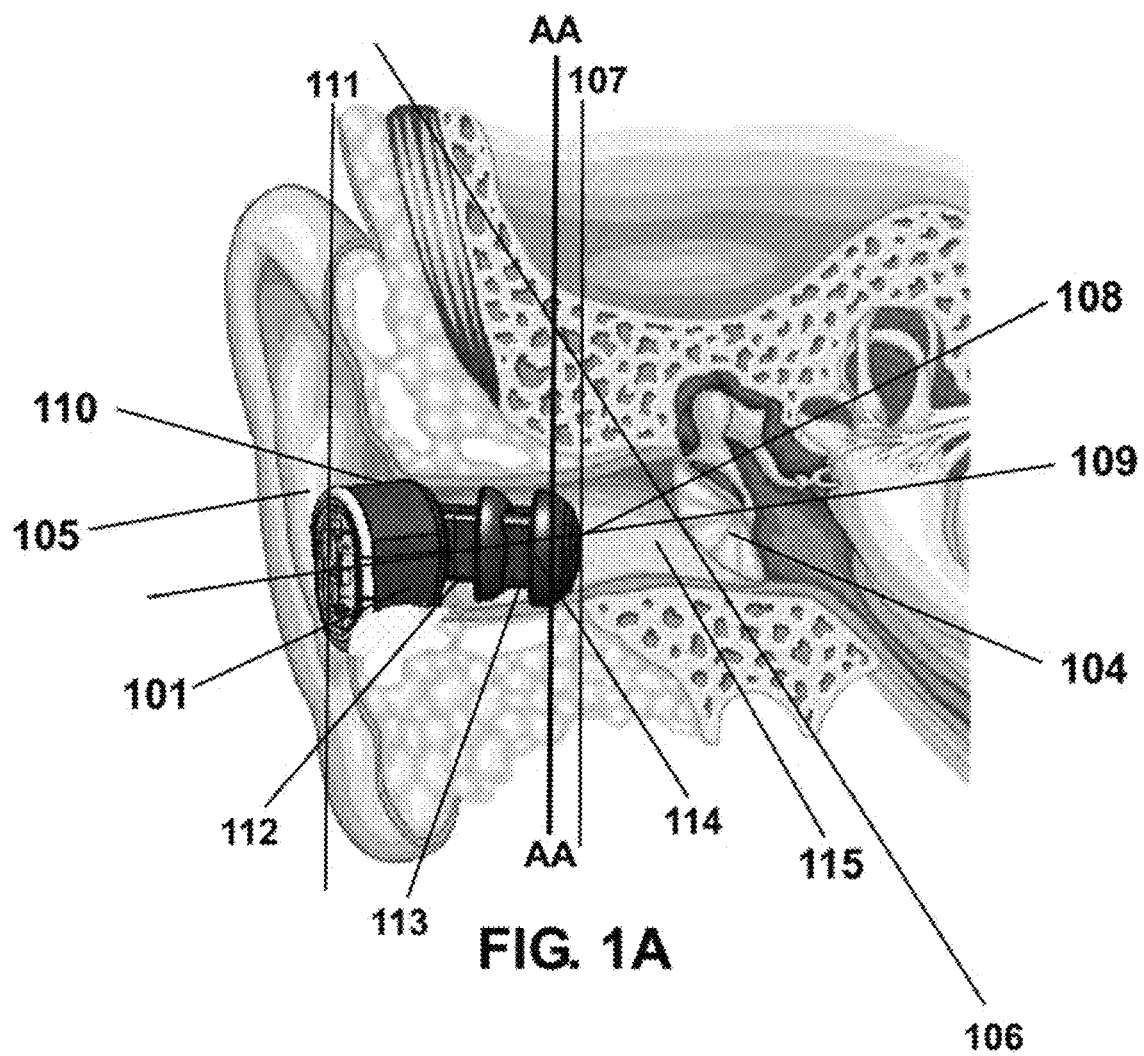
FIG. 1A illustrates an in-ear utility device 101 inserted into an ear 105, according to an embodiment of the invention.

Embodiments of the invention provide a wireless in-ear utility device having a speaker placed closer to the user's eardrum than conventional sound-delivery devices but not typically as close as some medically-regulated hearing aids. Embodiments of the in-ear utility device may be used for a variety of purposes and include a variety of electronic packages, such as for use as an amplified hearing device, for use as a music player, for use as a headphone device, and for use in various health-monitoring applications.

Embodiments of the invention provide a wireless in-ear utility device configured to have a variety of electronic packages. The electronic packages may serve a variety of functions, such as a Bluetooth device, a noise cancellation device that allows the user to focus on sounds of interest, a health-monitoring device, and a fitness device, each embodiment having the sensors and electronic configuration needed to carry out its mission. Embodiments of the wireless in-ear utility device may include an electronic package that supports the Internet of Things (IoT), defined as a network of physical objects embedded with electronics, software, sensors, and network connectivity, which enables the collection and exchange data between the in-ear utility device and other devices and/or the user. The Internet of Things allows objects to be sensed and controlled remotely across existing network infrastructure, allowing more direct integration between the physical world and computer-based systems.

The sensors of the in-ear utility device may perform a variety of functions. An accelerometer sensor 206*a* mounted in the body 210, for example, can be used to measure the user's steps. The ear (e.g., the ear 105 shown in FIG. 1A) is a stable location from which to make step count measurements since the head moves less independently from the legs than the arms (e.g., false positive step counts associated with wrist/arm borne accelerometers won't occur for people who make a lot of gestures with their arms while not otherwise moving). The accelerometer working with the processor 207 and the data repository 209 can detect motion indications indicative of a step. When a received motion matches the pattern for a step, then a step counter can be incremented. The accelerometer sensor, as discussed below, can also provide an operator alertness function, and the accelerometer sensor, as discussed below can also be used to provide a user interface based on tap detection.

Embodiments of the invention may provide a smart in-ear utility device that offers heightened and/or enhanced sounds for a variety of uses from a personal music player to a "walkie-talkie" type personal communicator. Embodiments of the invention may also provide an in-ear utility device that includes a wireless communications module that employs a wireless protocol so that the in-ear utility device may communicate with external devices, such as a mobile computing device, another in-ear utility device, a vehicle-borne computer, or a remote server or network, e.g., a cloud.

Embodiments of the invention may further provide an in-ear "smartphone," e.g., a smart device having functionality rivaling that of a smartphone but using user interfaces appropriate for an aural rather than a visual device, including but not limited to voice recognition technology. The "smartphone" embodiment of the in-ear utility device may also (or alternatively) include a visual user interface operating on some form of a computing platform, or a visual display device tethered to the in-ear utility device, according to an embodiment of the invention. The visual user interface does not have to comprise a "screen" but could be provided by some form of altered reality and/or virtual reality (AR-VR), according to an embodiment of the invention. The "smartphone" embodiment of the in-ear utility device may include an audio user interface, according to an embodiment of the invention.

Electronic component packages used in embodiments of the in-ear utility device may comprise, for example, microelectronic devices. Electronic components may include a microphone, an amplifier, a battery, a speaker, a wireless communications module, and/or any combination thereof. The electronic component package in some embodiments may include a processor (e.g., a CPU) and/or a data storage component. For example, the electronic component package 113 may include functionality for executing any number of software applications ("apps") and/or storing data such as media.

FIG. 1A illustrates an in-ear utility device 101 inserted into an ear 105, according to an embodiment of the invention. The in-ear utility device 101 includes an electronics package 113, such as the electronics component package 202 shown in FIG. 2A. Embodiments of the in-ear utility device 101 may include a speaker 108 disposed at the proximal tip 107 of the body of the in-ear utility device 101 and a microphone 110, disposed in the distal portion 111 of the in-ear utility device 101.

Some embodiments of the in-ear device 101 are designed to rest in the ear 105 between 8 to 12 mm. away from the user's tympanic membrane (eardrum) 104. Thus, the in-ear utility device 101 when placed properly in the ear canal 115 has a proximal tip 107 (along with the speaker 108) that lies from 8 to 12 mm. from the outer edge 106 of the eardrum 104 along a longitudinal axis 109, according to an embodiment of the invention. Studies have shown that the length of the typical human ear canal 115 varies from 27 mm to 35 mm measured along a curved center axis. Thus, embodiments of the in-ear utility device 101 reside well inside the ear canal 115.

The distance of the in-ear utility device 101 to a given user's eardrum 104 varies based on the depth of the user's ear canal 115. Some users have shallow ear canals while other users have deep ear canals. Therefore, the distance of the in-ear utility device 101 may vary in depth from user to user. The in-ear utility device 101 comprises a body 112 having the longitudinal axis 109 extending between a distal end 111 and a proximal tip 107. The distal end 111 of the in-ear utility device 101 resides just outside the user's ear 105 so that the in-ear utility device 101 may be easily removed by hand, according to an embodiment of the invention. In some embodiments of the invention, the in-ear utility device 101 might reside inside the ear canal 115 with no part of the device outside the ear 105.

In some embodiments, the speaker 108 may contact the eardrum 104 or be in even closer proximity to the eardrum than indicated in FIG. 1A, e.g., with the possible assistance of an audiologist. (The assistance of an audiologist is not normally needed for proper operation of the in-ear utility device 201.) In some embodiments of the invention, the in-ear utility device may reside in a broader range than 8 to 12 mm. from the user's eardrum 104, e.g., 3 mm. to 15 mm. The 8 to 12 mm. range, however, should provide improved sound quality to the user while also residing at a distance that does not require the employment of an audiologist to satisfy health and safety regulations.

In contrast with the in-ear utility device 101, conventional earbuds fit in the outer ear and face but are not inserted in the user's ear canal. Similarly, conventional in-ear headphones (e.g., in-ear monitors or IEMs) are inserted in the ear canal 115 but at a considerable distance (e.g., no closer than 20 mm away from the typical user's eardrum 104). Thus, the in-ear utility device 101 resides closer to the user's eardrum 104 than conventional headphones, earbuds, and in-ear headphones. Among other things, having the in-ear utility device 101 inserted in the user's ear canal 115 will aid in keeping the in-ear utility device 101 attached to the user even when the user is engaged in physically strenuous activities.

Figure 1B:
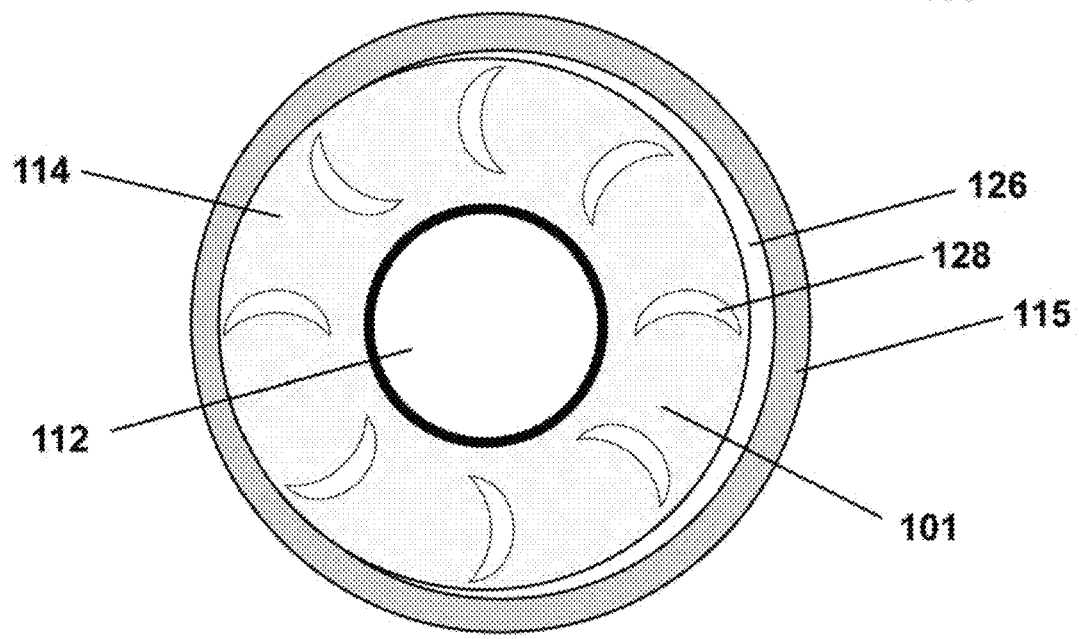
FIG. 1B illustrates a cross section taken along the line AA shown in FIG. 1A, according to an embodiment of the invention.

FIG. 1B illustrates a cross section taken along the line AA shown in FIG. 1A, according to an embodiment of the invention. As shown in FIG. 1B, in practical application, the in-ear utility device 101 is inserted into the ear canal 115 where it conforms to the shape of the ear canal 115. The typical use's ear canal 115 is not likely to comprise a perfect circle as shown in FIG. 1B.

The in-ear utility device 101 does not typically fill up the whole of the user's ear canal 115. One or more gaps 126 may occur between the in-ear utility device 101 and the ear canal 115. The gaps 126 may lower pressure in the user's ear canal 115.

The in-ear utility device 101 is typically covered with a seal or soft tip 114, and the in-ear utility device 101 typically touches the ear canal 115 at the points where the tip or seal 114 touches the ear canal 115 and possibly at the far outer entrance to the ear canal 115. The seal 114 might not cover portions of the in-ear utility device 101 outside the user's ear canal 115, according to an embodiment of the invention.

The seal 114 is configured to create gaps 126 between the in-ear utility device 101 and the ear canal 115, according to an embodiment of the invention. These gaps 126 not only lower pressure in the ear canal 115, the gaps also serve the additional purpose of allowing ambient sounds to pass through to the user's eardrum 104. Thus, a user wearing the in-ear utility device 101 can continue to experience ambient sounds in a natural manner (e.g., constant sound stimulus), and the user's own voice should sound normal to him/her. The ability to still hear ambient sounds naturally while wearing an ear-borne hearing device does not commonly occur with devices such as headphones and hearing aids. In addition, the in-ear utility device 101 not touching many points on the ear canal 115 should also increase user comfort and provide better heat transfer, allowing the in-ear utility device 101 to be worn for extended periods of time, according to an embodiment of the invention.

Studies show that the cross-sectional area in the middle portions of the typical human ear canal 115 range between 25 $mm^2$ and 70 $mm^2$. Thus, the embodiments of the seal 114 need to cover a fairly wide range of diameters. Thus, the seal 114 may be available in a variety of sizes, although the body 112 may be manufactured in a single size, according to an embodiment of the invention.

The seal 114 allows the portion of the body 112 that rests in the user's ear canal 115 to be narrower than the ear canal 115. Thus, the body 112 that contains the electronic package 113 does not typically touch the user's ear canal 115. The presence of the seal 114 protects the user against malfunctions of the electronics package 113. So, for example, if the battery (e.g., the battery 213 shown in FIG. 2A) happens to develop a short, the user should be protected from shock and heat because of the presence of the seal 114. The user is protected by the seal 114 in part because many embodiments of the seal 114 are constructed from a non-metallic material (i.e., lower heat transfer and possibly insulating).

The seal 114 may also include one or more slits 128 configured to relieve pressure in the user's ear canal 115, allowing the in-ear utility device 101 to be worn comfortably by the user for long periods of time. The slits 128 also provide the user with non-occluded aural access to ambient sounds outside the user's ear 105, according to an embodiment of the invention.

Thus, portions of the user's ear canal 115 remain non-occluded by the in-ear utility device 101 due, in part, to the slits 128 and the gaps 126. A user of the in-ear utility device 101 is typically able to hear sounds external to the in-ear utility device 101 and should also not suffer from increased pressure in the ear canal 115 due to the presence of the in-ear utility device 101 in the user's ear canal 115, as discussed above.

The material selection for the in-ear utility device 101 may facilitate the in-ear utility device 101 in entering the ear 105 while facilitating retention of the in-ear utility device 101 in the ear 105 for long periods of time (e.g. while exercising). Embodiments of the invention provide an in-ear utility device 101 covered in (e.g., the seal 114) (or composed of) a deformable material that is comfortable to wear for a long period of time and can be produced in bulk eliminating the need for customization. For example, the seal 114 covering the in-ear utility device 101 may be customized to account for variations in size of user's ear canals (e.g., small, medium, and large).

Figure 11:
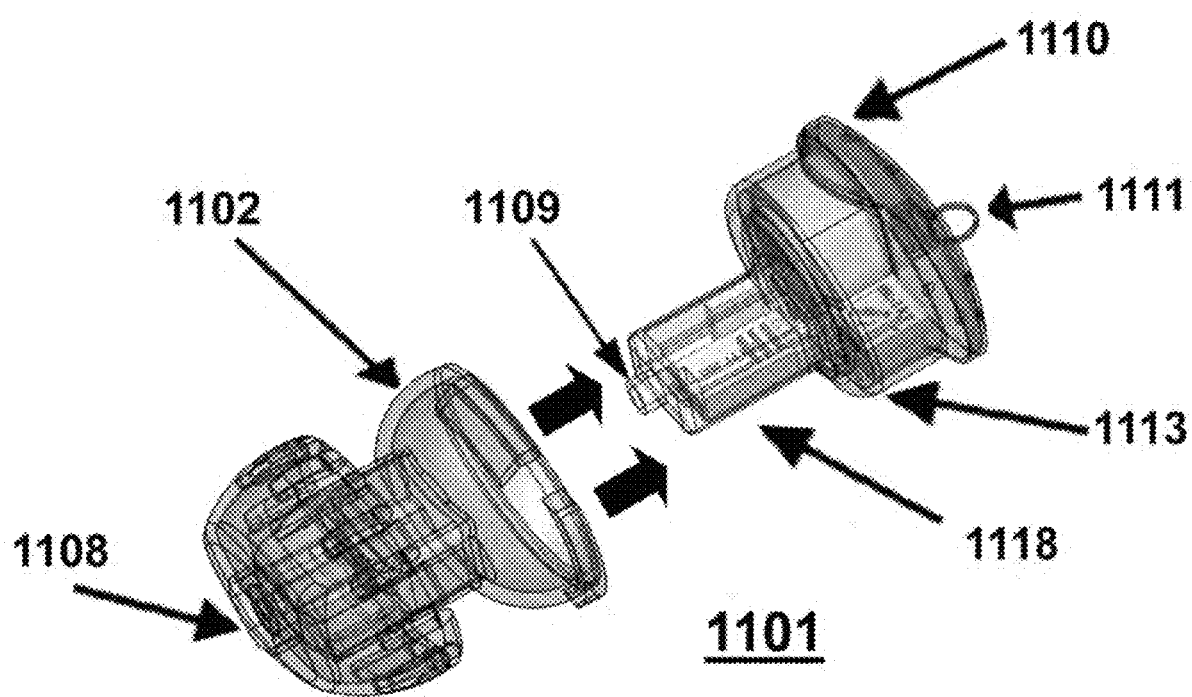
FIG. 11 illustrates an embodiment of an in-ear utility device 1101 configured as a single, integrated body rather than as a multi-pieced body as shown and described in FIG. 3.

The body 112 could comprise a variety of materials, including various metals. As noted above, the seal 114 protects the user's ear canal 115 from the body 112 of the in-ear utility device 101. In addition, as shown in FIG. 11, an embodiment of the invention may be extremely small (e.g., nano sized). The seal 114 may be formed of a material that has a Shore A Durometer hardness value of between 20-30. In an alternative embodiment of the invention, the body 112 of the in-ear utility device 101 itself may be formed of a material that has a Shore A Durometer hardness value of between 20-30. In such an embodiment, the body 112 serves a function similar to the seal 114.

An electronic component package 113 is fixed inside, mounted on, and/or embedded in or on the body 112 of the in-ear utility device 101 and includes electronic circuitry configured to allow the in-ear utility device 101 to be inserted into the user's ear canal 115 without damaging the in-ear utility device 101 or causing injury to the user's ear 105, according to an embodiment of the invention. The electronic component package 113 includes a speaker 108 at its proximal end 107, according to an embodiment of the invention. The seal 114 reduces the size available for the electronic component package 113. Thus, the specific components in the electronic component package 113 may need to be carefully selected for small size, in addition to other characteristics, according to an embodiment of the invention.

FIGS. 1A-1B illustrate an in-ear utility device 101 inserted into a human ear 105. Embodiments of the in-ear utility device 101 may be configured for non-human ears, such as other primates, other mammals, and even non-mammalian species. Components of the electronics component package and the elastic body would be sized accordingly in these embodiments of the invention.

Figure 2A:
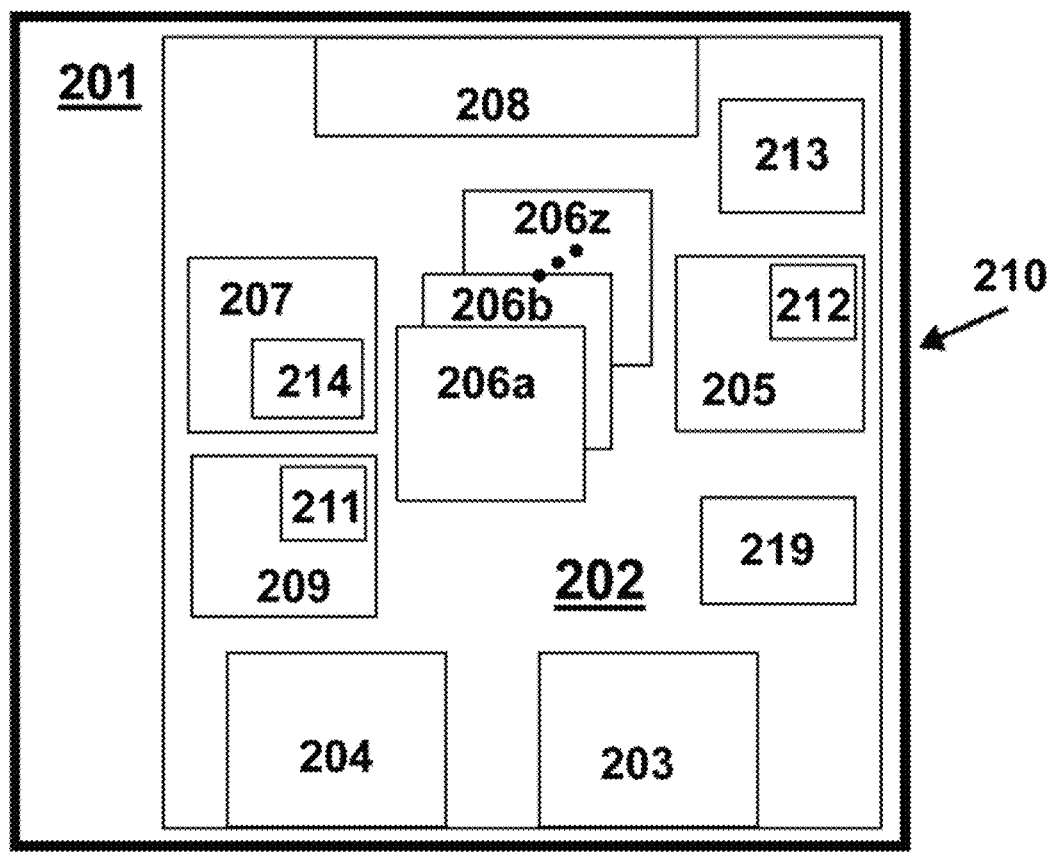
FIG. 2A provides a block diagram that illustrates an in-ear utility device 201, according to an embodiment of the invention.

FIG. 2A provides a block diagram that illustrates an in-ear utility device 201, according to an embodiment of the invention. The in-ear utility device 201 is formed of a body 210 that contains an electronic component package 202. The specific configuration of the electronic component package 202 may vary from embodiment to embodiment of the in-ear utility device 201, as discussed, for example, with respect to FIGS. 2B-11. In some embodiments, the in-ear utility device 201 may be on the order of about 5 mm. to 5 cm in length.

The body 210 may include a deformable seal (e.g., the seal 302 shown in FIG. 3) to allow the in-ear utility device 201 to be inserted into a user's ear canal (e.g., the ear canal 115 shown in FIG. 1A) without damaging the in-ear utility device 201 or causing harm to the user's ear (e.g. the ear 105 shown in FIG. 1A). The body 210 may be made in one size, and the covering seal (e.g. the seal 302 shown in FIG. 3) allows the in-ear utility device 201 to conform to a broad range of ear canal anatomies, according to an embodiment of the invention. The seal may have several different sizes, according to an embodiment of the invention.

Embodiments of the in-ear utility device 201 may be waterproof and worn in many environments, such as during swimming or while bathing. The in-ear utility device 201 may also be worn during sleep without discomfort. This may allow the in-ear utility device 201 to be utilized during many times when conventional sound devices may be uncomfortable, simply not work, or even be dangerous to use.

Electronic Component Package

The electronic component package 202 may include one or more electronic components such as a microphone 203, a wireless communications module (e.g., transceiver) 204, an amplifier 205, a battery 213, a processor 207, a speaker 208, a voice recognition chip 214, a Hall Effect sensor 219, and a data storage component 209, various sensors 206a-206z, according to an embodiment of the invention. The electronic component package 202 may include multiple copies of the same components, e.g., two microphones, either for backup purposes or to provide expanded capabilities. The individual components in the electronic component package 202 may be electrically coupled and/or wired as needed to provide conventional functionality for such components in a manner known to ordinarily skilled artisans, except when noted herein.

The small form factor for the in-ear utility device 201 typically requires the application of the smaller electronic components than the components typically found in other head-mounted devices, such as Bluetooth devices, according to an embodiment of the invention. The circuit connecting the electronic components suggests the application of flexible circuitry. Flexible electronics, also known as flex circuits, provide a means for assembling electronic circuits by mounting electronic devices on flexible plastic substrates, such as polyimide, PEEK, or transparent conductive polyester film. Additionally, flex circuits can be screen printed silver circuits on polyester. Flexible electronic assemblies may be manufactured using identical components used for more rigid printed circuit boards, allowing the board to conform to a desired shape, and/or to flex during its use.

Many types of electronic components may be employed in the in-ear utility device 201, as discussed above. For example, in various embodiments, the in-ear utility device may include microelectronics, nanoelectronics, micro-circuitry, nano-circuitry and combinations thereof, Microphone and Speaker The microphone 203 may communicate with the speaker 208. The microphone 203 may be in electronic and/or mechanical communication with the speaker 208. Sound/vibrations picked up by the microphone 203 may be transmitted to the speaker 208. In some embodiments, the sound/vibrations picked up may be amplified via the amplifier 205 and transmitted to the speaker 208. In various embodiments, the amplifier 205 may include a digital signal processor (DSP) 212. In various embodiments of the invention, the DSP 212 may perform (or assist in) a number of functions, such as noise cancellation and speech recognition. The DSP 212 need not be co-located with the amplifier 205, according to embodiments of the invention.

The microphone 203 may be a significantly stronger microphone than typically found in hear aid devices. For example, the microphone may operate in the range of 80 Hz to 5000 KHz, a range not typically found in hearing aids. The microphone 203 at this range detects sounds at a much lower decibel range than the typical hearing aid and essentially detects a whole spectrum of human hearing, according to an embodiment of the invention.

Because the processor 207 and the microphone 203 may be more powerful than similar components found in hearing aids, the in-ear utility device 201 may need to remove white noise generated by the processor 207, especially given the more powerful microphone 203 while noise removal can be accomplished by means of an appropriate audio filter.

A typical hearing aid microphone also operates at a comparatively low voltage such as 1.2V in comparison to the more powerful microphone 203 that operates at 3.5 to 5V. Thus, the circuitry inside the in-ear utility device 201 also needs to filter out white noise generated by its powerful electrical components, according to an embodiment of the invention.

The speaker 208 may be a significantly smaller speaker than typically found in Bluetooth devices. This smaller speaker 208 in combination with the smaller form factor of the body 210 allows the in-ear utility device 201 to penetrate farther into the user's ear canal than a Bluetooth device.

The microphone 203 does not need to communicate with the speaker 208, exclusively, or at all in various embodiments of the invention. The microphone 203 may be employed for tasks not directly connected with the speaker 208 and vice versa. In an embodiment of the invention, the microphone 203 communicates sounds to the processor 207, the DSP 212, and/or the voice recognition chip 214, and/or other apparatus to determine the type of environment that the user is located in (e.g., dense urban area, barren wilderness, etc.) and allow the processor 207 to make an appropriate action, depending on the task(s) set for the in-ear utility device 201.

The speaker 208 typically resides closer to the user's eardrum (e.g., the eardrum 104 shown in FIG. 1A) than the microphone 203 during operation. As shown in FIG. 1A, the speaker 108 is disposed at the proximal tip 107 of the body of the in-ear utility device 101 while the microphone 110 is disposed in the distal portion 111 of the in-ear utility device 101. The microphone 203 may be external to the ear, or closer to ear canal opening.

In some embodiments, the distance between the speaker 208 and the microphone 203 may range between from 5 mm to 5 cm. As a general matter, the greater the distance between the microphone 203 and the speaker 208, the lower likelihood of feedback between the microphone 203 and the speaker 208. The speaker 208 and the microphone 203 may be placed closer together if feedback between the components can be nullified or compensated for, according to an embodiment of the invention.

However, in some embodiments, the dimensions of the in-ear utility device 201 and/or the distance between the microphone 203 and the speaker 208 might be smaller and/or larger than the dimensions/distances provided above. For example, an embodiment of the invention may be prepared for users wearing helmets (e.g., as police officers, soldiers, football players, motorcyclists, and/or bicyclists). Similarly, an embodiment of the in-ear utility device 201 made for security personnel, hunters, etc. might be extended in size to accommodate additional microphones, or higher fidelity microphones, and/or enhanced communications equipment.

In embodiments, audio input to the speaker 208 may come from the wireless communications module 204, such as when the wireless communications module 204 is configured for Bluetooth® communications. Additionally, audio input to the speaker 208 may come from the data storage component 209 of the in-ear utility device 201. For example, playing stored music or instructions. These configurations may also include inputs from the microphone 203 but could occur without a microphone being included in the device.

Processor and Data Storage

In some embodiments, the in-ear utility device 201 includes a processor 207 which may be integral with the electronic component package 202 or operate under the control of a remote computing device (e.g., a mobile computing device) sending instructions via the communications module 204.

The processor 207 in the in-ear utility device 201 may access data and/or execute software applications 211, according to an embodiment of the invention. The data and software applications 211 may be stored in the data storage component 209 and/or delivered to the processor 207 via the communications module 204 from a remote storage device located away from the in-ear utility device 201. For example, the processor 207 might execute a software application that resides on a mobile phone linked to the in-ear utility device 201. A skilled artisan will appreciate that many software applications known in the art may be utilized by the processor 207. A variety of different data and software applications herein have been labeled 211, as an indication that the data and/or software applications are stored in the data storage component 209.

For example, the processor 207 may be configured with processor-executable instructions 211 to perform operations to distinguish meaningful sound, such as speech, from ambient noise. Such instructions may perform operations for receiving sound signals from the microphone 203, determining whether the sound signals represent meaningful sound, according to various criteria stored in the data storage component 209, providing the sounds to the speaker 208 when the sound signals represent meaningful sound, and filtering the sounds from the speaker 208 when the sound signals do not represent meaningful sound. Such instructions 211 for a speech detection program may be present in the data storage component 209 of the in-ear utility device 201 or a coupled external computing device.

The processor 207 may comprise a CPU, or a like computing device, or may alternatively comprise a simple circuit that directs the operations of the various components in the electronic component package 202, according to an embodiment of the invention. In embodiments in which the processor 207 comprises a simple control circuit, the other components in the electronic component package 202 may also be simple and/or few in number, e.g., just a battery 213, a data storage component 209, and a speaker 208, in addition to the processor 207.

In some embodiments, the processor 207 may be a significantly more powerful computing device than conventionally found in hearing aids. For example, the processor 207 might be a CSR8670 chip. CSR8670 is an audio system-on-chip (SoC) solution with wireless connectivity, embedded flash memory and integrated capacitive touch sensors. The CSR8670 includes noise cancellation and voice recognition capabilities. Thus, in some embodiments of the invention, the processor 207 may include some of the other components shown in FIG. 2A. In contrast, the typical completely-in-ear-canal (CIC) hearing aid (e.g., a hearing aid in the ear canal rather than behind the ear) uses an SB3229-E1 chip or similar processing chip, which has a slower speed and a smaller feature set than the processor 207. The processor 207 may require higher power than the typical hearing aid processor. The CSR8670 chip requires between 4V to 2.8V. The SB3229-E1 chip operates at much lower voltage, e.g., 1.2V. The CSR8670 chip operates at 20-34 milliamps while the SB3229-E1 chip operates in the micro-amps range. Thus, placing the processor 207 into the body 210 may require careful adjustment in order to operate properly, according to an embodiment of the invention. The filtering of white noise, for example, has already been mentioned.

The data storage component 209 may comprise a non-transitory memory, such as RAM, flash, ROM, hard drive, solid state, drive, optical media and the like. The data storage component 209 may include various types of data, such as media, music, software, and the like. The data storage component 209 may have a variety of sizes, e.g., 1 to 4 gigabytes, according to an embodiment of the invention. In-the-ear-canal (CIC) hearing aids, by comparison, typically have much smaller size memories. Integrating the data storage component 209 into the in-ear utility device 201 requires care to make sure that components function properly in the small form factor.

Wireless Communication Module

The wireless communications module 204 can be implemented using a combination of hardware (e.g., driver circuits, antennas, transceivers, modulators/demodulators, encoders/decoders, and other analog and/or digital signal processing circuits) and software components. Multiple different wireless communication protocols and associated hardware can be incorporated into the wireless communications module 204.

The wireless communications module 204 includes structural and functional components known in the art to facilitate wireless communication with another computing device or a remote network. The wireless communications module 204 can include RF transceiver components such as an antenna and supporting circuitry to enable data communication over a wireless medium, e.g., using Wi-Fi (IEEE 802.11 family standards), Bluetooth® (a family of standards promulgated by Bluetooth SIG, Inc.), or other protocols for wireless data communication. In some embodiments, the wireless communications module 204 can implement a short-range sensor (e.g., Bluetooth, BLE or ultra-wide band).

In some embodiments, the wireless communications module 204 can provide near-field communication ("NFC") capability, e.g., implementing the ISO/IEC 18092 standards or the like. NFC can support wireless data exchange between devices over a very short range (e.g., 20 centimeters or less). NFC typically involves a near field magnetic induction communication system that provides a short range wireless physical layer that communicates by coupling a tight, low-power, non-propagating magnetic field between devices. In such embodiments, the wireless communication module 204 may include a transmitter coil in the in-ear utility device 201 to modulate a magnetic field which is measured by means of a receiver coil in another device, e.g., another in-ear utility device or a smartphone. In some embodiments, the wireless communications module 204 can have an ultrasound transducer function, receiving ultrasound data communications and translating them into an electronic signal. Ultrasound communications may offer lower power than some other modes of wireless communications. The wireless communications module 204 may also be capable of translating an electronic signal into an ultrasound signal for transmission to another device, according to an embodiment of the invention.

In some embodiments of the invention, the in-ear utility device 201 can communicate bi-directionally via a network. In such embodiments, the wireless communications module 204 may comprise a Bluetooth® digital wireless protocol such that the in-ear utility device 201 may communicate with a remote computing device. Bluetooth® technology provides a low-cost communication link. The Bluetooth® transceiver in an embodiment of the wireless communications module 204 may be configured to establish a wireless data link with a suitably equipped mobile computing device and/or another in-ear utility device.

In an embodiment, the wireless communications module 204 of the in-ear utility device 201 may operate in conjunction with another in-ear utility device (e.g. one in-ear utility device in a left ear and another in-ear utility device in a right ear), while in another embodiment an in-ear utility device 201 may operate independently. In yet another embodiment, at least one in-ear utility device 201 may operate in conjunction with a mobile computing device.

Figure 10:
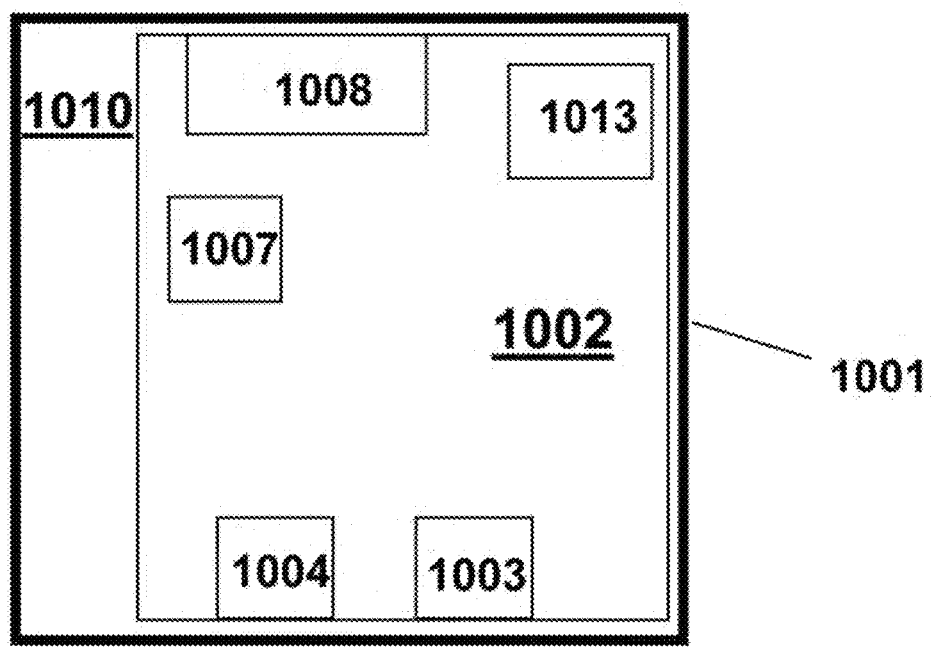
FIG. 10 illustrates an embodiment of an in-ear utility device 1001 configured to provide a walkie-talkie function (a portable, two-way radio transceiver), according to an embodiment of the invention.

As shown further in FIG. 10, the in-ear utility device 201 may operate as a walkie-talkie device communicating with another in-ear utility device operating in another ear of the user, with another device associated with the user, with another in-ear utility device associated with another user, and/or with a third-party device. In some embodiments, a user of the in-ear utility device 201 might be able to communicate with another in-ear utility device user using little more than just a whisper and at great distances.

The in-ear utility device 201 may also include functionality (e.g., the wireless communication module 204) to communicate bi-directionally via a long-range wireless network. In one embodiment, the long-range wireless network includes a cellular network. In another embodiment, the long-range wireless network includes a multimedia communications network. In another embodiment, the long-range wireless network includes wireless technologies such as Global System for Mobile Communications (GSM), Code Division Multiple Access-One (cdmaOne), Time Division Multiple Access (TDMA), PDC, Japan Digital Cellular (JDC), Universal Mobile Telecommunications System (UMTS), Code Division Multiple Access-2000 (cdma2000), and Digital Enhanced Cordless Telephony (DECT).

The wireless communications module 204 may be configured to communicate with a remote server or network. In one embodiment, the remote network is a cloud computing platform. As used herein, the term "remote computing device" or "mobile computing device" refers to anyone or all of cellular telephones, tablet computers, phablet computers, personal data assistants (PDAs), palm-top computers, notebook computers, laptop computers, personal computers, wireless electronic mail receivers and cellular telephone receivers (e.g., the Blackberry® and Treo® devices), multimedia Internet enabled cellular telephones (e.g., Blackberry Storm®), multimedia enabled smart phones (e.g., Android® and Apple iPhone®), and similar electronic devices that include a programmable processor, memory, a communication transceiver, and a display.

Sensors and Sensor Arrays

In embodiments, the in-ear utility device 201 may include one or more sensors 206a-206z configured to detect and/or measure various phenomena. In one embodiment, the in-ear utility device 201 may include one or more sensors 206a-206z configured to detect a physiological parameter of the user. Physiological parameters detected or measured by the sensors 206a-206z may include body temperature, pulse, heart rate, $VO_2$ Max (also known as maximal oxygen consumption), pulse oximetry data, respiratory rate, respiratory volume, maximum oxygen consumption, cardiac efficiency, heart rate variability, metabolic rate, blood pressure, EEG data, galvanic skin response data, and/or EKG/ECG. Thus, the sensors 206a-206z may detect, for example, the ambient temperature, humidity, motion, GPS/location, pressure, altitude and blood analytes such as glucose of the user of the in-ear utility device 201.

In an embodiment, the in-ear utility device 201 may include one or more sensors 206a-206z configured to detect the location or motion of the user, such as, for example an accelerometer, a GPS sensor, a gyroscope, a magnetometer, and/or a radiometer. In an embodiment, the in-ear utility device 201 may include a voice sensor 206a coupled to the microphone 203.

Specific sensor 206a-206z configurations may vary across embodiments of the in-ear utility device 201, e.g., one embodiment might include an ambient temperature sensor, a heart rate sensor, and a motion sensor while another embodiment includes a pressure sensor, a pulse sensor, and a GPS locator. The pulse sensor could be configured to reside on the in-ear utility device 201 in a position inside the user's ear canal and provide its readings to the processor 207. The pulse measurements could serve a variety of functions, including as input to a program for determining driver alertness, as discussed below.

The various sensor configurations may be configured to work together to measure various phenomena that may be used to trigger a particular action and/or the sensors may operate independently to trigger a variety of actions. Operations of the sensors 206a-206z may be aided by the processor 207 and processing instructions 211 stored in the data storage component 209 and/or instructions retrieved from a remote data source via the wireless communications module 204.

The in-ear utility device 201 may be configured to have an array of sensors 206a-206z configured to collect data. The data collected by the sensors 206a-206z may be data related to the user (e.g., biological data) and/or the user's environment (e.g., temperature, elevation, ambient noise). Such embodiments of the invention do not necessarily need to include sound processing devices (e.g., a microphone, a speaker, and/or an amplifier). The collected data may be processed by the processor 207 to provide services of use to the user and/or may be transmitted to a device external to the in-ear utility device 201.

Sensors for the in-ear utility device 201 may be provided in packages that include extra capacitors and extra insulators for a variety of health and safety reasons, according to an embodiment of invention. The sensors for the in-ear utility device 201 are typically intended for long-term in-the-ear usage, according to an embodiment of the invention. For example, the sensor packages in the in-ear utility device 201 may be configured such that if a given sensor shorts, the external temperature of the in-ear utility device 201 will not rise appreciably and the user will not receive a short, according to an embodiment of the invention.

Equipment Operator Alertness Sensor Array

The sensor(s) 206a-206z might include an accelerometer 206a configured to determine if an equipment operator (e.g., a car driver, a truck driver, a locomotive engineer, an airplane pilot, and/or a sea captain) or someone having a critical need for alertness (e.g., a security guard, a policeman, a surgeon, etc.) is sufficiently or appropriately alert to perform their assigned task.

For example, assume that a driver wearing the in-ear utility device 201 has fallen asleep while driving and/or is inappropriately alert (e.g., the driver's head is bobbing up and down), the accelerometer can send an appropriate signal to the processor 207 that executes a safety program 211. The accelerometer 206a may, for example, be configured to measure movement of the user's head position (see, e.g., FIG. 2C), and the processor 207 can use these measurements to determine the operator's alertness. Based on the signal from the accelerometer 206a and instructions/data in the safety program 211 (e.g., an alertness application), the processor 207 may determine to take an appropriate remedial action (e.g., sound a warning through the speaker 208). An in-ear utility device 201 could be configured solely for this function (e.g., no music playing capabilities). Such an embodiment of the invention does not necessarily require an amplifier and/or a microphone. Alternatively, the in-ear utility device 201 could be configured to perform a variety of functions.

The safety program 211 could be designed in a number of ways and many existing operator safety programs already exist. The safety program 211 could, for example, receive sensor inputs in addition to the accelerometer input and integrate the results to form an accurate assessment of the operator's overall alertness state. The safety program 211 could also measure the frequency with which the accelerometer 206a reports the driver's head bobbing up and down. If the driver's head bobs up and down X times per minute for some number of minutes, the driver could be warned and/or an alarm could be sounded, and/or a third party could be alerted, and/or the vehicle could park itself, assuming the vehicle had capabilities for self-parking or some other stand-down mode.

The processor 207 might also use the wireless communication module 204 to send relevant data to another device about the alertness state of the driver wearing the in-ear utility device 201. So, for example, the wireless communication module 204 might send driver alertness data (and/or alarm states) to a wireless computing device associated with the vehicle controlled by the wearer of the in-ear utility device 201. Depending on the capabilities of the vehicle, the vehicle might opt to engage its own safety program, such as taking control of the vehicle away from the driver and then parking the vehicle by the side of the road. The processor 207 may send the driver data to a remote location (e.g., a trucking company's offices and/or an insurance companies offices) for remote data processing (e.g., tracking which drivers from a fleet of drivers have the greatest tendencies for nodding off while driving).

The sensors 206a-206z may also include sensors that can assist the processor 207 determine who is wearing the in-ear utility device 201. So, for example, the data repository 209 might include biometric data 211 related to the user of the in-ear utility device 201. If the processor 207 has determined that the user of the in-ear utility device 201 is operating heavy equipment, for example, then the sensors 206a-206z, including the accelerometer, may be configured to track various actions and alertness states of the user. The in-ear utility device 201 may use the communication module 204 to communicate driver information with another device (e.g., the vehicle and/or a nearby smartphone) and then prevent the user from hearing certain things while operating the vehicle. So, for example the vehicle's own safety program might prevent the user from hearing Facebook posts while operating the vehicle. The safety program might be configured to prevent everything but emergency messages from reaching the user of the in-ear utility device 201 while the vehicle is in operation and controlled by the user.

The accelerometer may also be used to determine if the user of the in-ear utility device 201 has suffered a strong shock and/or fallen down. When the processor 207 receives a signal from the accelerometer that matches a pattern for a shock (e.g., fall pattern data 211 stored in the data storage component 209), then the processor 207 may take an appropriate action. So, for example, the processor 207 might instruct the playing of a safety check audio file 211 stored in the data storage component 209 through the microphone 208. The processor 207 might also instruct that the fall condition be transmitted to a distant device (e.g., one operated by a security or health-monitoring company) via the communications module 204.

Sensor for Turning In-Ear Utility Device On/Off

The in-ear utility device 201 may include a Hall Effect sensor 219 that is configured to determine if the in-ear utility device 201 has been inserted into a charging case (e.g., the charging case 1200 shown in FIG. 12A), and if so, then the processor 207 turns off the in-ear utility device 201 (e.g., the Hall Effect sensor 219 acts as a switch), according to an embodiment of the invention.

The Hall Effect sensor 219 includes a transducer that varies its output voltage in response to a magnetic field. The Hall Effect sensor 219 can provide proximity switching, positioning, current sensing applications for the in-ear utility device 201 in connection with a charging case or charging station for the in-ear utility device 201. The Hall Effect sensor 219 can be used to provide a means for recharging the in-ear utility device 201 without the in-ear utility device 201 necessarily needing to have a physical on/off switch, and by shutting down the in-ear utility device 201 provides a means for faster recharging of the battery 213 by the charging case or charging station, according to an embodiment of the invention.

The Hall Effect sensor 219 may be configured to detect the magnetic field of the charging case or charging station as the in-ear utility device 201 is being placed into the recharging device. So, for example, the Hall Effect sensor 219 may detect the charging case at a distance of one-half inch (12.7 mm.), and the processor 207 may direct electronic components of the in-ear utility device 201 to shut down, according to an embodiment of the invention. An embodiment of a charging case is shown in FIGS. 12A-12D.

The Hall Effect sensor 219 also allows the in-ear utility device 201 to have a smaller and more stream-lined form factor than might otherwise be the case—in addition to providing a more efficient means for recharging the battery 213. Hall Effect sensors are not conventionally found in Bluetooth devices or in hearing aids. The process of using the Hall Effect sensor 219 to turn off the in-ear utility device 201 may be reversed when the in-ear utility device 201 is removed from the charging case, according to an embodiment of the invention.

Alarm, Notification, and Verification Functions

In another embodiment, the in-ear utility device 201 may provide various alarm and notification functions. For example, the in-ear utility device 201 may be utilized as an alarm clock. This functionality could be provided by the processor 207 and/or the processor 207 coupled with the data storage device 209 and/or the processor 207 coupled with the communications module 204 and a third device (e.g., a mobile phone). An ordinary artisan should know how to make the processor 207 provide an alarm function. In addition, the processor 207 in conjunction, for example, with data 211 stored in the data storage component 209 may provide a calendar function, a timer function, a stopwatch function, and/or a reminder function. Similarly, the processor 207 in combination with data 211 from the data storage component 209 combined with data from various sensors 206a-206z may provide various alarm and/or warning functions, e.g., a heart attack warning or a high blood pressure warning. Likewise, in conjunction with the communications module 204, the sensors 206a-206z could provide various alarms to various third parties remote from the in-ear utility device 201. For example, if the in-ear utility device 201 was equipped with one or more accelerometers 206a, then a third party could be automatically notified of an event such as a car crash, a bicycle crash, and/or a fall.

The in-ear utility device 201 can also be configured to provide various forms of authentication. Authentication may be provided in a number of ways, including but not limited to application of voice recognition processes known in the art. For example, the microphone 203 in combination with the DSP 212, the processor 207, and the data storage component 209 using voice data 211 can provide authentication of the authorized user(s) of the in-ear utility device 201. The user could provide a voice sample detected by the microphone 203 that is provided to the processor 207 that then retrieves the voice data 211 and compares the voice sample against the voice data 211. The processor 207 (possibly in conjunction with the DSP 212) analyzes the received voice sample and determines if the current user's voice matches the voice data 211. This electrical component combination could be used to determine when the in-ear utility device 201 has been stolen or otherwise being operated by an unauthorized person. As mentioned above, the processor 207 could be a simple control circuit configured for the authentication function rather than a processor chip configured to control the authentication function. The authentication function could also be used to verify the user before delivering sensitive information through the speaker 208.

In an alternative embodiment, authentication may be performed outside the in-ear utility device 201 via an external device such as a smartphone. In such an embodiment, the authentication function for the in-ear utility device 201 comprises the microphone 203 and the communications module 204 to perform the authentication function in a manner similar to the process described above for an organic authentication function.

User Interface for In-Ear Utility Device

Sensors, and combinations of sensors 206a-206z, may also be used to provide a user interface function for the in-ear utility device 201. For example, an accelerometer 206a (or a G-force sensor) might activate when a user moves or taps his/her hand (or by the user shaking his/her head while wearing an ear-borne accelerometer in the in-ear utility device) in a predetermined manner (e.g., taps of a certain force or intensity within a certain time frame or head nods of certain characteristics) that can be sensed by the accelerometer sensor 206a. Such an action could trigger the accelerometer sensor 206a such that additional commands might be received through additional actions such as further tapping or by head shaking.

For example, a user might tap his/her jaw, ear, cheek, neck, or another pre-designated location (e.g., via a predesignated single tap, double tap, or triple tap). This tapping action could trigger the accelerometer sensor 206a such that additional commands could also be received through additional taps. So, for example, once the G-force sensor 206a has been activated, then two more taps might activate a music player (e.g., the music player described in FIG. 8) or cause a music selection to be forwarded by some number of seconds. The taps detected by the accelerometer 206a could be delivered to the processor 207 that may retrieve additional data 211 from the data storage component 209. The user's selection could be confirmed by appropriate auditory confirmation (e.g., confirmatory audio message) delivered through the speaker 208. The processor 207 could retrieve an appropriate confirmatory audio message 211 from the data storage component 209 and deliver it to the speaker 208. Choices made by the user as well as possible command selections could be confirmed (e.g., spoken) to the user via the speaker 208 through the use of one or more confirmatory audio messages. Similar sensor configurations 206a-206z could also be used for user input functions, such as accelerometers, pulse rate, and temperature sensors.

Figure 2B:
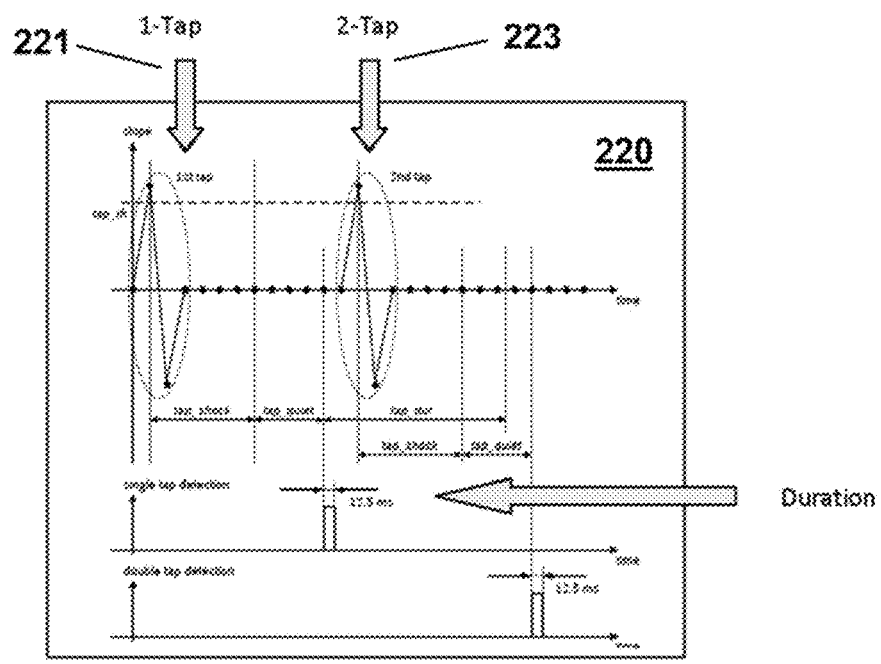
FIG. 2B provides a diagram 220 that shows a shock provided by a first tap 221 and the shock provided by a second tap 223 as measured by an accelerometer sensor 206a in an in-ear sound device 201, according to an embodiment of the invention.

FIG. 2B provides a diagram 220 that shows a shock (of a certain intensity) provided by a first tap 221 and the shock (of a similar intensity) provided by a second tap 223 as measured by an accelerometer sensor 206a in an in-ear sound device 201, according to an embodiment of the invention. As shown in FIG. 2B, the taps 221, 223 have a tap intensity and a time duration within the predetermined range for a tap command recognizable by the in-ear utility device 201 and also include a predetermined quiet period between the taps 221, 223, according to an embodiment. The tap time duration and the quiet period represent a predetermined command convention established by the in-ear utility device 201 for recognizing taps as commands and not ignoring them as being merely random shocks. (Of course, the accelerometer 206a might record all shocks and report them to the processor 207 for another purpose.)

The accelerometer sensor 206a passes its data to the processor 207 shown in FIG. 2A, and the processor 207 compares the received data against relevant command data 211 (e.g., a predetermined pattern) stored in the data storage component 209. If the taps 221, 223 match an appropriate predetermined pattern (e.g., a pattern for predetermined action command or predetermined on/off command), then the processor 207 engages an appropriate action (e.g., sends an action signal), such as turning on/off the in-ear utility device 201 and/or performing another task (e.g., a predetermined action command). For example, a representative tap sequence could perform an audio profile selection command that causes the processor 207 to select a given audio profile from the data storage component 209, such as the audio profiles discussed herein. In some embodiments of the invention, the processor 207 may access a confirmatory audio message 211 stored in the data storage component 209 and play the confirmatory audio message through the speaker 208 before engaging any action as a means for determining that the user's tap and/or head nod command has been properly interpreted by the processor 207.

The accelerometer sensor 206a might communicate tap data to the processor 207 using inter-integrated circuit (I2C) communications, according to an embodiment of the invention. I2C is typically a multi-master, multi-slave, single-ended, serial computer bus that is typically used for attaching lower-speed peripheral integrated circuits (e.g., the accelerometer sensor 206a) to processors and microcontrollers, such as the processor 207. Such communications use binary code with a unique address through one programmed input/output (PIO). PIO is a method of transferring data between a CPU (e.g., the processor 207) and a peripheral (e.g., the accelerometer 206a). Other electric components and sensors 206a-206z of the in-ear utility device 201 may also use I2C for internal communications, according to an embodiment of invention.

Figure 2C:
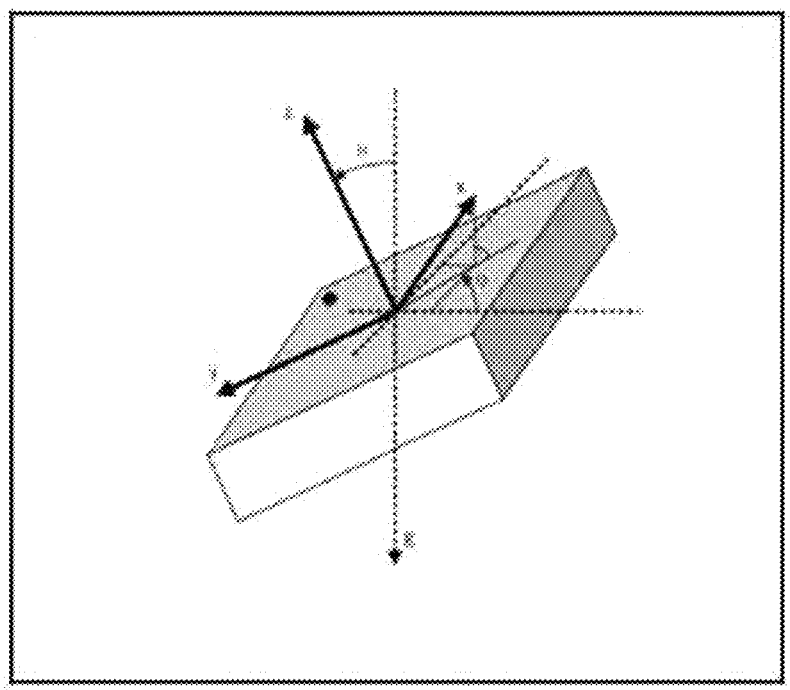
FIG. 2C provides a geometrical representation of tap sensing in which the taps are based on distance/tap events/time frame/coordinate, according to an embodiment of the invention.

FIG. 2C provides a geometrical representation of tap sensing in which the taps are based on distance/tap events/time frame/coordinate, according to an embodiment of the invention. Tap sensing has functional similarity with a common loop touch-pad or clicking keys of a computer mouse or tapping on a surface at a specific location, according to an embodiment of the invention. A tap event is detected if a pre-defined slope of the acceleration of the least one axis is exceeded. Two different tap events can be distinguished: A "single tap" is a single event within a certain time (e.g., the tap 221 shown in FIG. 2B), followed by a certain quiet time. A "double tap" consists of a first such event (e.g., the tap 221) followed by a second event within a defined time frame (e.g., the tap 223 shown in FIG. 2B).

The orientation recognition feature of the accelerometer 206a provides information about an orientation change of the accelerometer 206a with respect to the gravitational field vector 'g', as shown in FIG. 2C. The measured acceleration vector components with respect to the gravitational field are defined as shown in FIG. 2C. Therefore, the magnitudes of the acceleration vectors may be calculated as follows:

$$acc\_x = 1 \text{ g} \times \sin\Theta \times \cos\varphi$$

$$acc\_y = -1 \text{ g} \times \sin\Theta \times \sin\varphi$$

$$acc\_z = 1 \text{ g} \times \cos\Theta$$

$$acc\_y/acc\_x = -\tan\varphi$$

Depending on the magnitudes of the acceleration vectors the orientation of the in-ear utility device 201 in space is determined and stored in an orientation vector. For example, there may be three orientation calculation modes with different thresholds for switching between different orientations: symmetrical, high-asymmetrical, and low-asymmetrical. Additional operational characteristics for the accelerometer 206a may be found in manuals, such as BMA222E, Digital, Triaxial Acceleration Sensor for the Bosch Sensortec manufactured by Bosch, which is incorporated by reference herein.

In some embodiments of the invention, in the tap sensor user interface, the accelerometer sensor 206a sends the processor 207 a communication sequence at periodic intervals that contain received tap data. In other embodiments of the invention, the tap sensor user interface may be driven by tap events, e.g., the accelerometer communicates nothing until a tap occurs.

A user interface for the electronic component package 202 shown in FIG. 2A, including the sensors 206a-206z, could also be provided to the user via the wireless communications module 204 and an external device, such as a mobile phone or a computer, according to an embodiment of the invention. A voice command user interface could also be provided via the microphone 203 and the processor 207, according to an embodiment of the invention. A voice command user interface could also be provided via the voice recognition chip 214 applied in combination with the microphone 203 with additional data 211 from the data storage component 209 and the processor 207, as well as hybrid user interfaces that combine the tap user interface discussed above with a user interface hosted on a visual device, such as a smartphone. An ordinary artisan should understand how to configure these various user interfaces.

The user interface could be provided on a remote device (e.g., a smartphone) with a subset of commands provided by an audio interface in the in-ear utility device 201. So, for example, commands such as "fast forward" in a music playing apparatus could be engaged through the tap user interface with more complicated tasks, such as music genre selection, coming from a graphical user interface on a remote device (e.g., a smartphone).

On/Off Sensor Array for In-Ear Utility Device

Figure 2D:
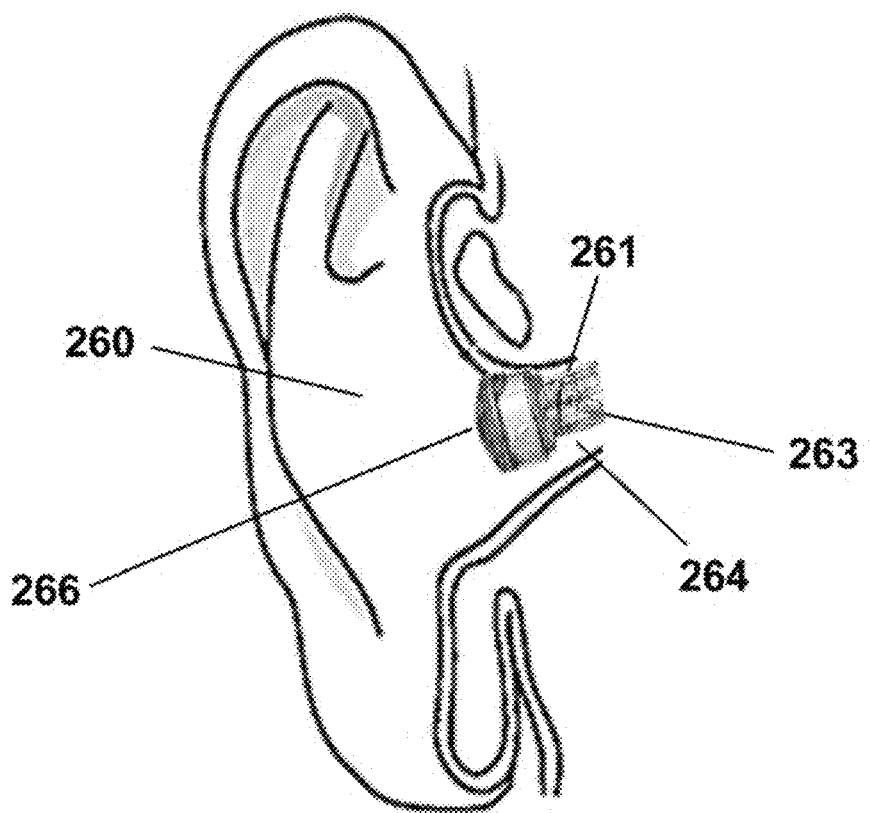
FIG. 2D illustrates a first humidity sensor 261 and a second humidity sensor 266 that provides a means for turning an in-ear utility device 263 on/off and/or components of the in-ear utility device 263 using relative changes in humidity, according to an embodiment of the invention.

FIG. 2D illustrates a first humidity sensor 261 and a second humidity sensor 266 that provides a means for turning on/off an in-ear utility device 263 and/or turning on/off components of the in-ear utility device using relative changes in humidity between the two humidity sensors 261, 266, according to an embodiment of the invention. The two sensors 261, 266 (e.g., the sensors 206a-206b shown in FIG. 2A) operate in conjunction with the processor 207 shown in FIG. 2A. The in-ear utility device 263 may be identical to the in-ear utility device 201, according to an embodiment of the invention.

The ear canal 264 typically has a different humidity than the ambient humidity outside the ear 267. The ear canal 264 is typically more humid and warmer than the ambient environment outside the ear, but in any event, the two humidities typically differ. Thus, when the humidity in a user's ear canal 264 differs from the humidity outside the ear 267, then the processor 207 can conclude that the user is wearing the in-ear utility device 263 (e.g., that the in-ear utility device 263 is donned or worn). Similarly, when the humidity in a user's ear canal 264 matches the humidity outside the ear 267, then the processor 207 can conclude that the user is not wearing the in-ear utility device 263 (e.g., that the in-ear utility device 263 is not worn or doffed). So, for example, assume that the data threshold trigger for the humidity sensors 261, 266 occurs within the range of a 30% congruence in humidity as measured by the sensors 261, 266, according to an embodiment of the invention.

When the processor 207 receives an indication (e.g., based on receipt of the humidity data from the humidity sensors 261, 266) that the humidity readings have changed to levels indicating that the in-ear utility device 261 has been removed from the ear, then the processor 207 engages an appropriate action; e.g. the in-ear utility device 261 shuts down, or particular components of the in-ear utility device shut down, and/or the in-ear utility device 261 switches to a lower energy state, and/or the in-ear utility device 261 attempts to confirm with the user (e.g., via the speaker 208) that the in-ear utility device 261 is no longer in the ear, according to an embodiment of the invention. When the in-ear utility device 263 is turned off, then the battery 213 could still provide minimal power to the humidity sensor 266 and the humidity sensor 261 and the processor 207. If the humidity sensor 266 and/or the humidity sensor 261 detect changes in humidity indicative of the in-ear utility device 263 being put in the user's ear canal 264, then the processor 207 can take an appropriate action, e.g., directing the battery to provide power to more components of the in-ear utility device 263.

Figure 2E:
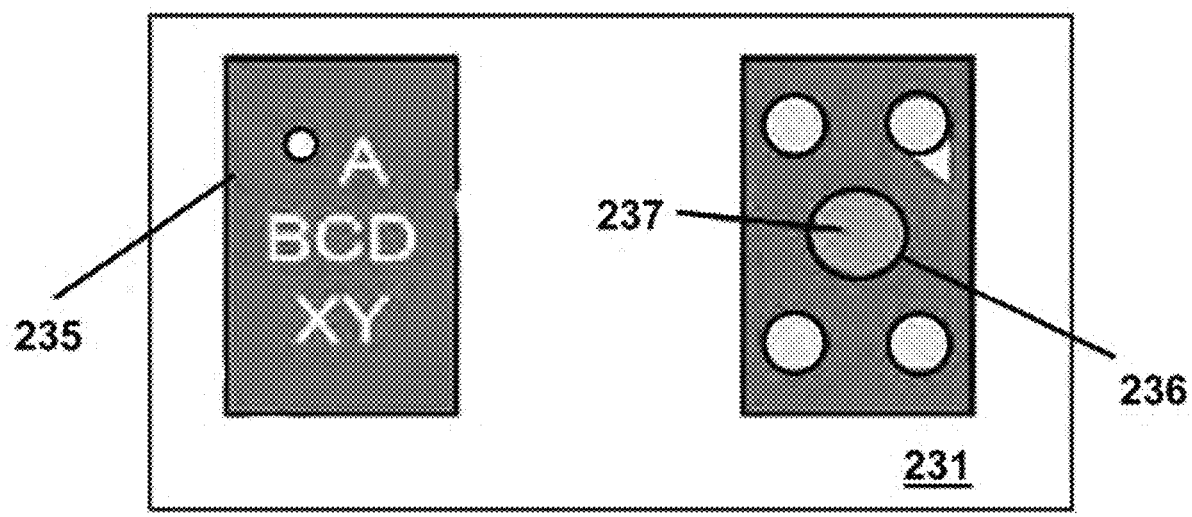
FIG. 2E illustrates a sensor array 231 that provides a means for turning the in-ear utility device and/or components of the in-ear utility device on/off using relative changes in temperature and humidity, according to an embodiment of the invention.

FIG. 2E illustrates a sensor array 231 that provides an alternative means for turning an in-ear utility device on/off using relative changes in temperature and humidity, according to an embodiment of the invention. The sensor array 231 comprises two sensors (e.g., the sensors 206a-206b shown in FIG. 2A) that operate in conjunction with the processor 207 shown in FIG. 2A.

The sensor array 231 comprises a temperature sensor 235 and a humidity sensor 236. The humidity sensor 236 includes a sensor window 237 that samples environmental humidity (e.g., humidity in the ear canal 115 shown in FIG. 1A). The temperature sensor 235 and the humidity sensor 236 employ I2C data communications (discussed above) to communicate temperature and humidity data to the in-ear utility device processor (e.g., the processor 207), according to an embodiment of the invention. The sensors 235, 236 may also use PIO to communicate data to the processor.

The human ear is generally more humid and warmer than the typical ambient environment outside the ear. Thus, a positive change in temperature and humidity on a relative scale provides an indication that the in-ear utility device 261 has gone from not being worn to be worn by a user. Similarly, the reverse indicates that the user has removed the in-ear utility device 261. So, for example, assume that the data threshold triggers for the temperature chip 235 and the humidity sensor 236 are within the range of a 30% to 70% change in humidity or temperature, according to an embodiment of the invention. As discussed and shown in FIG. 2D, a similar on/off function can be constructed using two humidity sensors at different locations rather than a paired temperature and humidity sensor, according to an embodiment of the invention.

The temperature chip 235 can be configured to monitor the user's body temperature. The temperature chip 235 resides inside the user's ear canal (e.g., the ear canal 115 shown in FIG. 1). A typical human's ear canal may include a variety of temperatures, depending on how close to the tympanic membrane (e.g., the tympanic membrane 104 shown in FIG. 1A), with temperatures near the tympanic membrane typically warmer than temperatures at the outer end of the ear canal. Near the tympanic membrane the temperature may be 99 degrees Fahrenheit (37 degrees Celsius) while in the middle of the ear canal temperatures may be range from 95-98 degrees Fahrenheit (34-36 degrees Celsius) while at the outer end of the canal may range in temperatures from 60 to 90 degrees Fahrenheit (16 to 32 Celsius).

When the processor 207 receives an indication that the temperature has changed to levels indicating that the user of the in-ear utility device 261 has a temperature beyond normal measures (e.g. a fever), then the processor 207 engages an appropriate action; e.g. the in-ear utility device 261 sends an audio message 211 (retrieved from the data storage component 209) through the speaker 208 to the user, according to an embodiment of the invention. The in-ear utility device 261 could also send temperature data to an external device via the communications module 204, according to an embodiment of the invention. Thus, the temperature chip 235 essentially provides a fixed thermometer in the user's ear canal and could essentially serve as a first warning to the user of an ill health condition (e.g., becoming too hot while exercising and/or having a fever due to a cold).

Figure 2F:
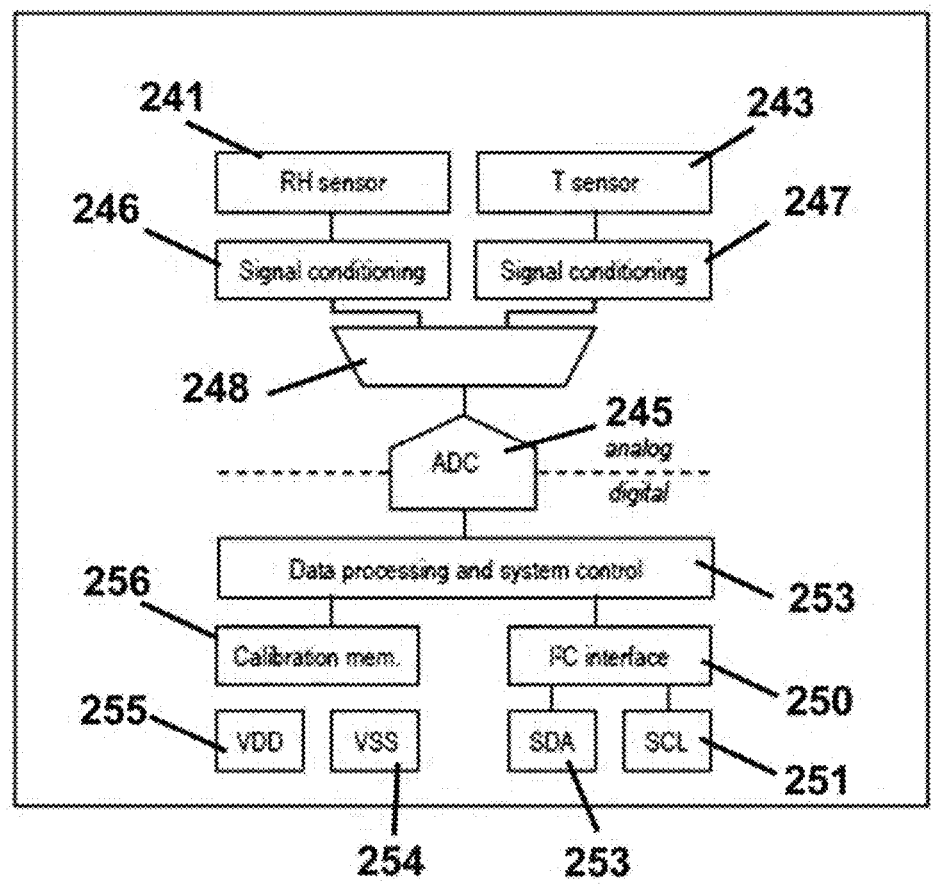
FIG. 2F illustrates how the output from a relative humidity sensor 241 and the output from a temperature sensor 243 can be provided to a processor, such as the processor 207 shown in FIG. 2A, according to an embodiment of the invention.

FIG. 2F illustrates how the output from a relative humidity sensor 241 and the output from a temperature sensor 243 can be provided to a processor, such as the processor 207 shown in FIG. 2A, according to an embodiment of the invention. Assume, for example, that measurements from the relative humidity sensor 241 and the temperature sensor 243 undergo respective amounts of signal conditioning 246, 247 before being combined into a single data stream.

Assume further that the relative humidity sensor 241 and the temperature sensor 243 provide their outputs in analog form. Thus, the combined output from the sensors 241, 243 passes through an analog-to-digital convertor 245 prior to being provided to a data processing and system control unit 253 (e.g., the processor 207 shown in FIG. 2A), according to an embodiment of the invention. The processor may then provide the data to various subcomponents and/or take an appropriate action based on the data received. As discussed above, on/off function could be configured using humidity sensors placed at different location on the in-ear utility device. In such an embodiment, the inputs shown in FIG. 2F for the temperature sensor might likely not be present because the temperature sensor would not be needed.

Figure 3:
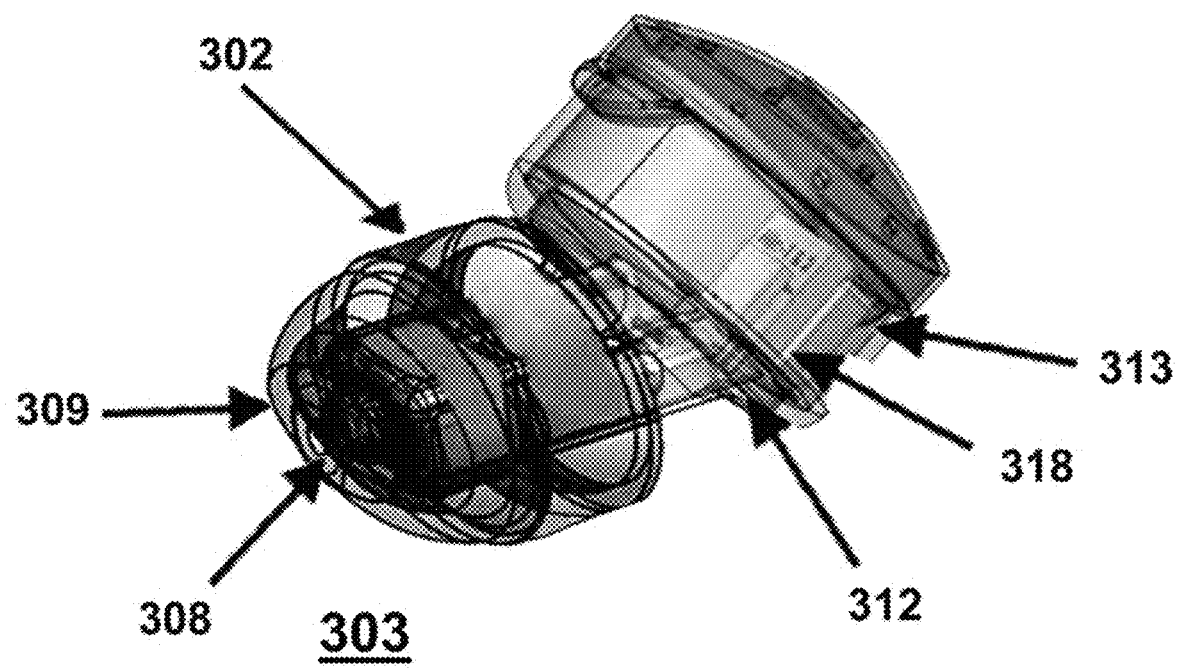
FIG. 3 illustrates an in-ear utility device 303 having a flexible seal 302 that covers a portion of the in-ear utility device 303 that is inserted into a user's ear canal (e.g., the ear canal 115 shown in FIG. 1A) during normal use, according to an embodiment of the invention.

FIG. 3 illustrates an in-ear utility device 303 having a flexible seal 302 that covers a portion of the in-ear utility device 303 that is inserted into a user's ear canal (e.g., the ear canal 115 shown in FIG. 1A and FIG. 1B) during normal use, according to an embodiment of the invention.

Embodiments of the invention provide the in-ear utility device 303 covered, or partially covered, with the seal 302 that is comfortable to wear for a long period of time. The external seal 302 deforms when the in-ear utility device 303 is inserted into a user's ear canal (e.g., the ear canal 115 shown in FIG. 1A) without damaging the in-ear utility device 303 or causing harm to the user's ear (e.g., the ear 105 shown in FIG. 1A). The deformable seal 302 cushions the user's ear canal (e.g., the ear canal 115 shown in FIG. 1A) from the material of the in-ear utility device's body 318.

The seals 302 can be produced in bulk eliminating the need for customizing the body 318 of the in-ear utility device 303. The seal 302 allows the in-ear utility device 303 and its body 318 to be "one size fits all" and conform to a broad range of ear canal anatomies, according to an embodiment of the invention. The seal 302 may be produced in several sizes (e.g., small, medium, larger) to accommodate differences in the size of human ear canals (e.g., the ear canal 115 shown in FIG. 1A). The seal 302 may even be produced in more customized sizes (e.g., from a mold or a measurement) due to the variability in human ear canal sizes.

The seal 302 needs to be comfortable for the user in order for the user to be able to wear the in-ear utility device 303 for long periods of time. Comfort from the seal 302 comes from making the seal 302 in a size that fits well into the user's ear canal. Comfort for the seal 302 also comes from making the seals from a flexible and soft material.

The seal 302 can be fabricated from many resilient polymeric materials known in the art, according to an embodiment of the invention. There are many known resilient polymeric materials that may be used to form the in-ear utility device 303 and/or its components, such as the seal 302. For example, natural rubber, neoprene rubber, SBR rubber (styrene block copolymer compounds), silicone rubber, EPDM rubber, polybutadiene rubber, polyvinylchloride elastomers, polyurethane elastomers, ethylene vinyls, acetate elastomers, elastomers based on acrylic acid precursors and vinyhalide polymers may all be generally suitable materials which can be used to provide the necessary softness for the seal 302. The seal 302 covering the in-ear utility device 303 is formed of a material that has a Shore A Durometer hardness value (by a technique such as ASTM 2240-81) of between 20-30, according to an embodiment of the invention.

The seal 302 allows the portion of the body 318 that rests in the user's ear canal (e.g., the ear canal 115 shown in FIG. 1A and FIG. 1B) to be narrower than the ear canal. Thus, the body 318 that contains the electronic component package 313 does not typically touch the user's ear canal. The presence of the seal 302 protects the user against malfunctions of the electronic component package 313. So, for example, if the battery (e.g., the battery 213 shown in FIG. 2A) happens to develop a short, the user should be protected from shock and heat because of the presence of the seal 302. The user is protected by the seal 302 in part because many embodiments of the seal 302 are constructed from a non-metallic material (i.e., lower heat transfer and possibly insulating).

The electronic component package 313 may include a speaker 309 disposed at the proximal tip 308 of the in-ear utility device 303. The electronic component package 313 is embedded in the body 318 of the in-ear utility device 303 and includes electronic circuitry configured to perform a variety of tasks and user-engaged functions, including the tasks described in FIGS. 1-2, 4-11.

The in-ear utility device 303 may also include one or more microphone ports (e.g., the microphone port 512 shown in FIG. 5A) to facilitate receipt of sounds into the in-ear utility device 303, according to an embodiment of the invention. The microphone port 512 is further disclosed in conjunction with FIGS. 5A-5C.

Embodiments of the in-ear utility device 303 have no wires protruding from the body 318 and no external behind-the-ear components. The in-ear utility device 303 may be used by the hearing impaired population as well as the general public. Thus, the in-ear utility device 303 may be used for sound amplification and communication purposes as well as a number of additional purposes as discussed herein.

The in-ear utility device 303 may also include a joint 312 that swivels to facilitate insertion of the in-ear utility device 303 in the user's ear, according to an embodiment of the invention. The joint 312 is described further in FIGS. 6A-6C.

Figure 4:
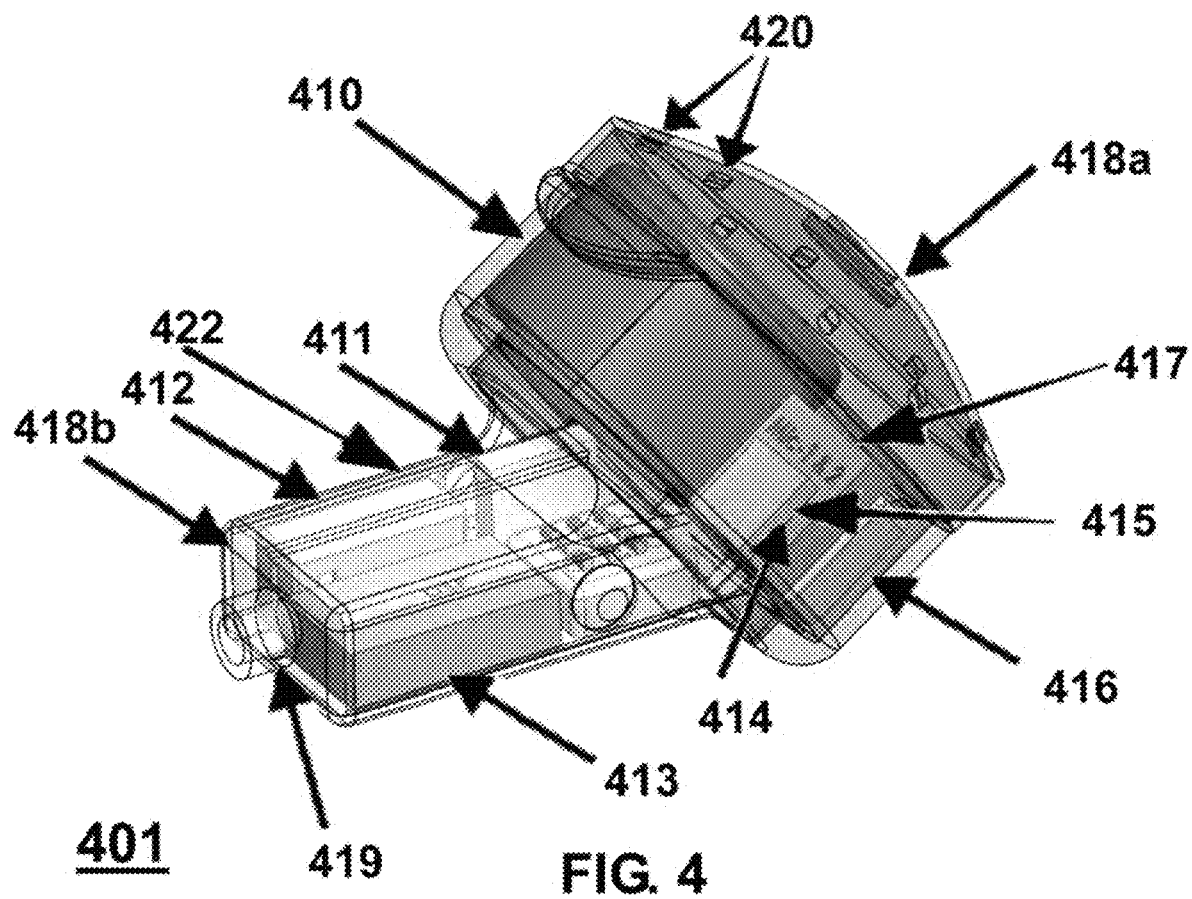
FIG. 4 illustrates an in-ear utility device 401 with its deformable seals removed, according to an embodiment of the invention.

FIG. 4 illustrates an in-ear utility device 401 with its deformable seal removed, according to an embodiment of the invention. As discussed in FIG. 3, the in-ear utility device 302 may include a deformable seal 302 for the portion of the in-ear utility device 303 (e.g., an in-ear portion 418b for the in-ear utility device 401) that enters the user's ear.

The in-ear utility device 401 comprises an electronic components package 422 that includes a battery 410, a power booster 411, a communications module (e.g., transceiver) 412, a DSP chip 413, a first microphone 414, a second microphone 415, a voice recognition chip 416, and a noise cancellation chip 417 that provides noise cancellation for the first microphone 414 and/or the second microphone 415, and a speaker 419, according to an embodiment of the invention.

The first microphone 414 may deliver sound to the speaker 419. The first microphone 414 may be in electronic and/or mechanical communication with the speaker 419. Sound/vibrations picked up by the first microphone 414 may be transmitted to the speaker 419 (directly and/or after various forms of signal processing have been applied to improve the quality of the signal). In some embodiments, the sound/vibrations detected by the first microphone 414 may be amplified via an amplifier, such as the amplifier 205 shown in FIG. 2A, and transmitted to the speaker 419. In some embodiments, the amplifier operates in conjunction with the digital signal processing (DSP) 413.

The microphones 414, 415 can be used for amplification for the hearing impaired. Various embodiments of the in-ear sound device 401 can be configured to determine which sound sources the user and/or an application 211 run by the processor (e.g., the processor 207 shown in FIG. 2A) wants to amplify. If the sounds to be amplified are all sounds in the in-ear utility device's environment, then it makes sense to amplify the signal from the ambient noise microphone 415. If the in-ear utility device 401 is configured to amplify the sound from the person(s) to whom the user of the in-ear sound utility device 401 are talking to, then the in-ear utility device 401 would amplify the signal from the voice microphone 414 since it will be more focused on picking up sounds from the direction that the wearer of the in-ear utility device 401 is facing. This process works well regardless of whether the in-ear utility device 401 is trying to perform noise cancellation based on the ambient microphone 415. The in-ear utility device 401 can have multiple modes for directional amplification such that the in-ear utility device 401 can switch among them depending on the situation. The user of the in-ear utility device 401 may have an actuator that allows the user to switch between modes. The actuator may be engaged by the tap sensor user interface discussed herein and/or by a visual user interface on a host device, according to an embodiment of the invention. The actuator may comprise a user-selectable actuator that could be applied to many embodiments of the invention.

In some embodiments of the invention, the distance between the speaker 419 and microphone ports 420 may be at a distance from 15 mm to 5 cm. The distance may need to be adjusted to avoid feedback, depending on the specific components that are used. As a general matter, the greater the distance between the microphone ports 420 and the speaker 419, the lower likelihood of feedback between the microphone ports 420 and the speaker 419.

The power booster 411 supplies additional electrical potential (e.g., 1.4 volts) in order to boost (or amplify) to a higher voltage (e.g., 3 volts) the voltage provided by the battery 410 to supply power to components of the in-ear utility device 401 that require higher voltage to operate properly, according to an embodiment of the invention. As mentioned, power demands for embodiments of the in-ear utility device operate at higher power than a conventional hearing aid.

Voice Recognition and Ambient Sound

The first microphone 414 may focus on picking up the voice of the user more strongly than the ambient sound microphone 415 while the second microphone 415 may be focused on detecting ambient sound, according to an embodiment of the invention. One or more voice focused ports for receiving sounds input to the first microphone 414 may reside in a number of locations on the in-ear utility device 401, such a voice focused port 512 shown in FIG. 5A.

The voice recognition chip 416 may be configured to perform operations to distinguish the user's voice from ambient noise. The voice recognition chip 416 may receive sound signals from the first microphone 414, determine whether the sound signals represent the user's voice, activate the speaker 419 when the sound signals represent meaningful sound, and filter the sounds delivered to the speaker 419 when the sound signals do not represent meaningful sound.

The voice recognition chip 416 may receive inputs from the first microphone 414 and/or the second microphone 415, according to an embodiment of the invention. As an alternative, the in-ear utility device 401 may include a processor, such as the processor 207 shown in FIG. 2A that has been configured to execute a program 211 that performs operations to distinguish meaningful sound from ambient noise.

The voice recognition chip 416 (or similar functionality) may be configured to engage a phone call, such as answering an incoming phone call and/or placing a new call, according to an embodiment of the invention. The voice recognition chip 416 may also provide a capability for disengaging a phone call as well. Similarly, the accelerometer sensor 206a in conjunction with the tap user interface may be used to provide a capability for engaging/disengaging telephony functions, according to an embodiment of the invention. Telephony functions can also be engaged through an application on a remote device, such as a smartphone, according to an embodiment of the invention.

Noise Cancellation

The noise cancellation chip 417 filters unwanted ambient noise prior to filtering the sounds into the first microphone 414 and/or a second microphone 415. The noise cancellation chip 417 may otherwise operate in a conventional manner.

Figure 5A:
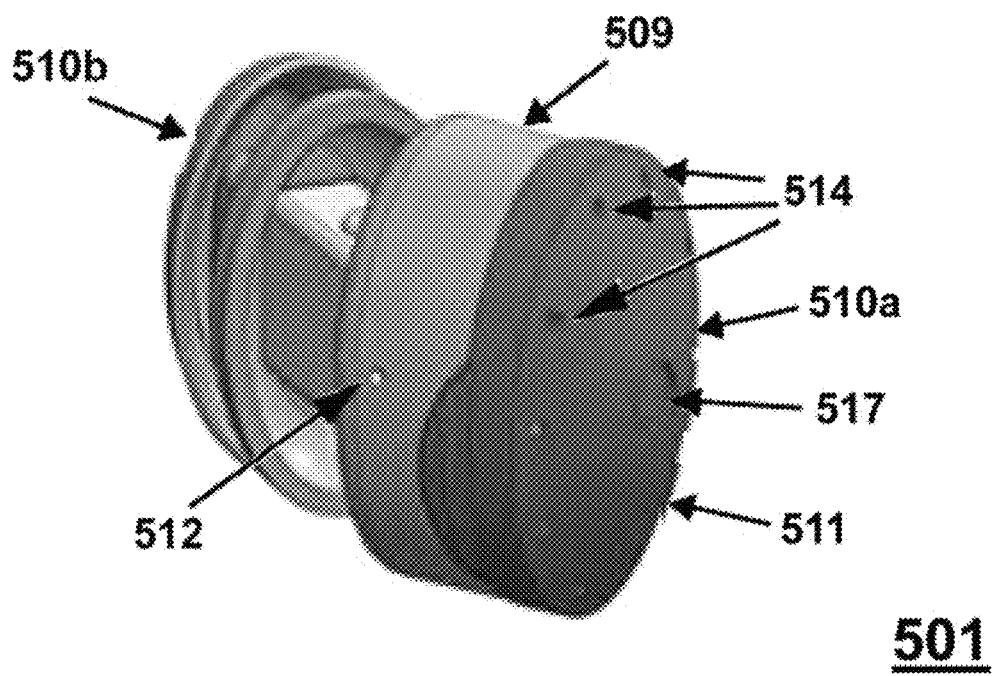
FIGS. 5A-5B illustrate an in-ear utility device 501 inserted into an ear canal 515, according to an embodiment of the invention.
Figure 5B:
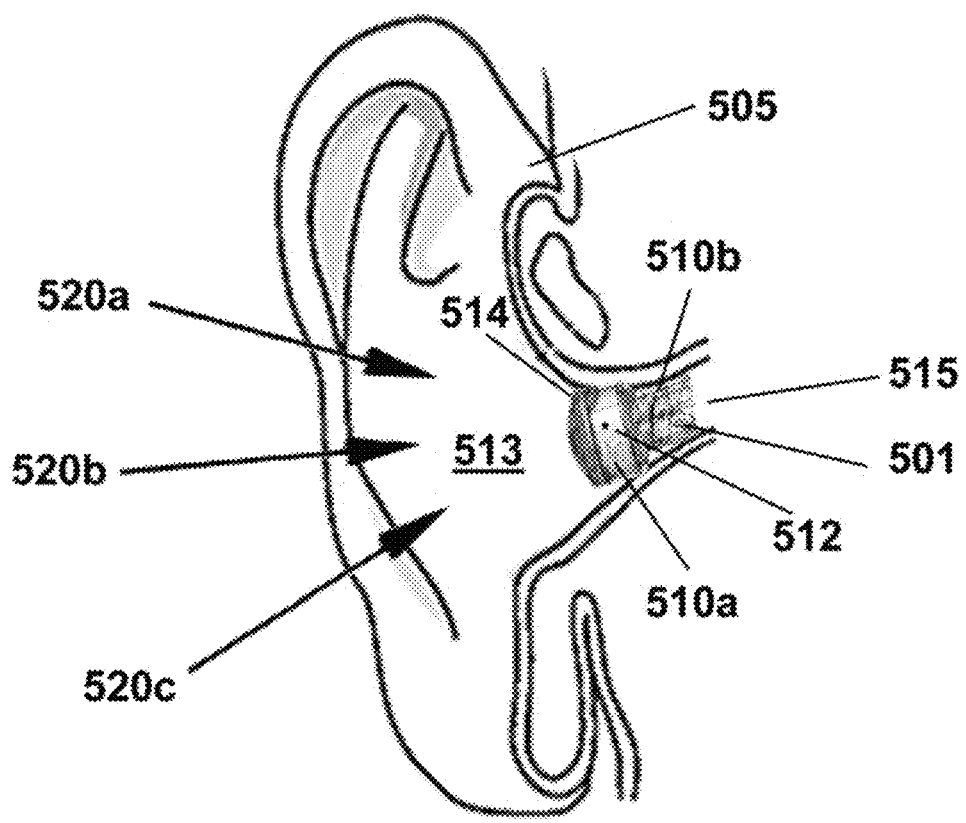
Figure 5C:
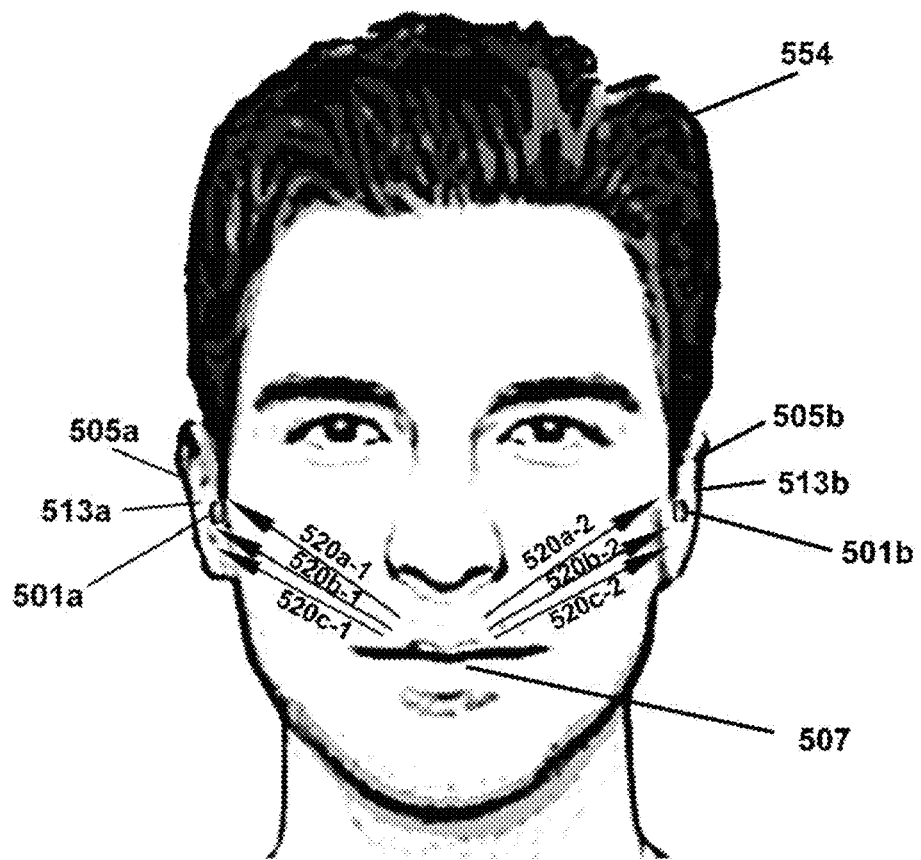
FIG. 5C illustrates a portion of the distal ends of two in-ear utility devices 501*a*, 501*b* in a single user's ears 505*a*, 505*b*, according to an embodiment of the invention.

As shown in FIGS. 5A-5C, an in-ear utility device 501 includes microphone input ports 512, 514 that take advantage of reflections from various parts of the human ear (e.g., the pinna and the conchae bowl) to ensure that the voice focused microphone (e.g., the first microphone 414) has a stronger component of relevant voice sound relative to the ambient noise microphone (e.g., the second microphone 415) that itself will have a stronger component of ambient noise. This difference between the two signals can be used by existing signal processing techniques (e.g., using the processor 207 and/or the DSP 413) to cancel the ambient noise and thereby optimize the sound quality of the voice data, according to an embodiment of the invention.

By using multiple microphone types for the first and second microphones 414, 415, such as an omnidirectional microphone and a directional microphone, the in-ear utility device 401 can exploit the spatial diversity of the speech and noise relying on spatial information about relative position of speech of interest and the competing noise. Thereby, subtracting the noise from the noisy speech. Thus, the first microphone 414 may comprise an omnidirectional microphone in some embodiments, and the second microphone 415 may comprise a directional microphone in some embodiments.

For embodiments of the invention in which two in-ear utility devices coordinate their efforts (see, e.g., FIG. 5C), each in-ear utility device 401 may have in each ear (e.g., the ear 105 shown in FIG. 1A) a directional microphone (e.g., the first microphone 414) facing toward the user's mouth (see, e.g., FIGS. 5A-5B) and an omnidirectional microphone (e.g., the second microphone 415) that captures sound from all directions. In such an embodiment, the in-ear utility device 401 may either use the first directional microphone (e.g., the microphone 414) to pick up the user's speech or subtract sound coming from the directional microphone from the omnidirectional microphone (e.g., the second microphone 415) and that should give better information about sounds coming from in front of the user. Even though the second microphone 415 is an omnidirectional microphone (capturing sound from 360 degrees), due to the location of the microphone (i.e. at entrance of ear canal), it will still see the pinna effect discussed below. This means that sound coming from behind the user will be attenuated and sound from the user's front will be amplified.

The in-ear utility device 401 may employ conventional noise cancellation techniques that are unrelated to the number of microphones and are based on spectral analysis of the signal and determining which parts of the signal that appears likely to be noise. Conventional noise cancellation processes employ the scientific certainty that a sound wave and its inverse cancel each other out. Conventional software, including available open source software, allows noise cancellations systems to take two copies of an audio clip, invert one of them, generate a third clip by mixing the two together and the third clip will be silent. This is how conventional active noise cancellation methods operate, by carefully blending the voice microphone signal with the inverted ambient noise signal making the appropriate adjustments for amplitude, etc. using various conventional signal processing techniques. These functions may be carried out by the processor (e.g., the processor 207 shown in FIG. 2A) if not dedicated hardware.

In performing voice recognition, the in-ear utility device 401 may retain some ambient sound and not filter all of it out before delivering a combined sound signal to the speaker 419. In other words, the user will likely want to retain some ambient sound for the user to hear in order to be fully aware of his environment.

As described further in FIGS. 5A-5C, many different noise cancellation methods can be employed in the in-ear utility device 401, according to an embodiment of the invention. Among other things, if the user wears an in-ear utility device 401 in the left ear and another in-ear utility device in the right ear, then the two in-ear utility devices can share audio data collected by their respective microphones and work together to improve voice recognition and/or improve noise cancellation, according to an embodiment of the invention.

The electronics components package 422 may include other combinations of electronic components and additional components (as discussed in FIGS. 1-3, 5-11), according to an embodiment of the invention. For example, the in-ear utility device 401 may also include a processor and a memory device such as the processor 207 and the data storage device 209, shown in FIG. 2A, and/or including one or more sensors 206a-206z, according to an embodiment of the invention. Among other things, the processor using data and instructions from the data storage device may perform noise cancellation and/or various enhancement techniques.

The in-ear utility device 401 may also include a swivel joint (e.g., the swivel joint 603 shown in FIG. 6) that connects an out-of-ear portion 418a and the in-ear portion 418b allowing the out-of-ear portion 418a to have a different orientation than the in-ear portion 418b, according to an embodiment of the invention. The ability of the out-of-ear portion 418a to have a different orientation from the in-the-ear portion 418b may aid in fitting the in-ear utility device 401 into the ear of a user (e.g., the ear 105 shown in FIG. 1A). The in-ear utility device 401 may include more swivels than just a single joint 603, according to an embodiment of the invention. As shown in FIG. 11, the in-ear utility device may alternatively comprise a single piece, according to an embodiment of the invention.

As shown in FIGS. 5A-5B, one or more voice focused port(s) 512 may channel detected sounds to a microphone focused on picking up the voice of the user more strongly than the ambient sound (e.g., the first microphone 414 shown in FIG. 4), according to an embodiment of the invention. The voice focused port(s) 512 may reside on a side 509 of a cap end 511 of the in-ear utility device 501, according to an embodiment of the invention. The side 509 resides on an out-of-ear portion 510a of the in-ear utility device 501 that corresponds to out-of-ear portion 418a shown in FIG. 4. The in-ear utility device 501 is shaped such that when inserted into the user's ear canal 515 the voice focused port 512 will rest facing outward or forward in alignment with the user's eyes and mouth, as shown in FIG. 5B.

As previously discussed, in some embodiments the port 512 may be located inside the user's ear canal 515. FIG. 5B illustrates an in-ear utility device 501 inserted into an ear canal 515, according to an embodiment of the invention.

Voice recognition using the voice focused port 512 takes advantage of the microphone input port location being a fixed distance from the user's voice when the user is speaking. As shown in FIG. 5B, a second portion 510b of the in-ear utility device 501 (shown here only partially) is inserted into the user's ear canal 515 during normal operation. The first portion 510a of the in-ear utility device 501 having the voice focused port 512 remains outside the user's ear during operation but fixed in position because of the anchoring of the second portion 510b in the user's ear canal 515, according to an embodiment of the invention.

A fixed distance from the voice focused port 512 to the user's mouth 507 is useful because this fixed distance helps in setting the spectral and intensity profile of the user's voice for voice recognition purposes and therefore easier to pick out the user's voice from the incoming audio signal. Therefore, the fixed distance can improve the signal-to-noise ratio even in noisy environments.

Changing the distance between the microphone input port and the input signal affects the signal-to-noise ratio of the captured sound. Moreover, in a reverberant room, the distance between the speaker and the microphone could also affect the spectrogram of the recorded sound. Therefore, the fact that the in-ear utility device 501 is always recording the user's voice from a fixed distance makes the speech recognition easier and more accurate.

The in-ear utility device 501 shown in FIG. 5A has been configured for insertion into a user's left ear. This orientation means that the voice focused port 512 shown in FIG. 5A would face the user's mouth in normal operation, as shown in FIG. 5B. Thus, the voice focused port 512 would be appropriate for the in-ear utility device 501b shown in FIG. 5C.

The in-ear utility device 501 includes at least one ambient noise port 514, according to an embodiment of the invention. The in-ear utility device 501 may even include multiple ambient noise ports 514 (e.g., more than 10 such ports), according to an embodiment of the invention. The ambient noise ports 514 may be disposed around the exterior of the cap end 511 of the in-ear utility device 501 in a 360 degree pattern from the center point 517 of the cap end 511 on the outer surface of the in-ear utility device 501, according to an embodiment of the invention.

Among other things, the ambient noise port(s) 514 can support the voice recognition process by helping cancel out unwanted frequencies in the manner previously discussed. The ambient noise port(s) 514 may provide input to a microphone, such as the second microphone 415 shown in FIG. 4, according to an embodiment of the invention. The ambient noise port(s) 514 aid in calibrating the direction of sounds 520a-520c entering the in-ear utility device 501 via the pinna 513 of the ear 505. The pinna 513, or conchae bowl, provides a horn, of sorts, that aids in naturally focusing the sounds 520a-520c. The location of the ambient noise port(s) 514 has been selected to facilitate its operation by advantageously exploiting the natural focusing and amplification provide by the pinna 513.

Due to the placement of the microphone ports 512, 514 the signal from the user's voice is amplified much more than ambient sound, especially given the anatomy of the human ear to which the in-ear utility device makes advantageous use of. The pinna 513 has evolved as a tool for enhancing and amplifying sounds having a pitch that is typical for a human voice while leaving most other frequencies untouched. Moreover, sounds which are coming from the front of the user sound louder than sounds coming behind the user due, in part, to the construction of the ear. Thus, the in-ear sound device 501 has been developed to advantageously apply the natural condition of the ear 505 and the pinna 513. This gives the in-ear sound device 501 the added benefit that the sound from the user's voice sound much louder than any sounds coming from behind the user, among other things.

Embodiments of the in-ear utility device 501 may employ directional microphones. Thus, the microphone 414 shown in FIG. 4 and the second microphone 415 shown in FIG. 4 may be directional microphones. As discussed with regard to the microphone ports 512, 514, one of these ports, the voice focused port 512 is specifically aimed at the user, and the ambient noise port(s) 514 are aimed straight in the vicinity of the speaker. Depending on whether the in-ear utility device 501 wants to focus on the user's voice or the sounds coming to the user and the user's environment, the signals from each of the microphones 414, 415 can be subtracted from each other, and the signal from the microphone that is of interest can be amplified.

The fact that one of the microphone input ports is in the ear canal 515 allows for cues from the pinna 515 which can be applied for front/back localization by the processor (or combination of equipment performing the sound processing functions). Moreover, use of directional microphones may also help in front/back localization of the speaker of interest. In addition, using of the right in-ear utility device 505a and the left in-ear utility device 505b (discussed in FIG. 5C) improves sound localization of right/left differentiation.

The microphone ports 512, 514 could be placed in a variety of locations on the in-ear utility device 501. The microphone ports 512, 514 could even be located inside the portion of the in-ear utility device 501 that resides in the user's ear canal 515. One microphone port, for example, could face inward to the user's ear canal, which facilitates determining when the user is speaking. The in-ear utility device 501 could even include a bone conduction microphone. In some embodiments of the invention, the ambient noise port(s) 514 could be replaced with a signal port, such as the embodiment shown in FIGS. 5F-5H.

Many different noise cancellation methods can be employed in the in-ear utility device 501, as discussed in conjunction with FIG. 4. Among other things, if the user wears an in-ear utility device 501 in the left ear and another in-ear utility device in the right ear (as shown in FIG. 5C), then the two in-ear utility devices 501a, 501b can be configured to work together to improve speech recognition and/or improve noise cancellation, according to an embodiment of the invention. On some occasions, the user of the in-ear utility device 501 may simply want to use the in-ear utility device 501 to cancel all the sound around himself and not hear any speech.

For example, left/right sound localization cues in the horizontal are obtained from interaural level differences and interaural time differences between the right ear 501a and left ear 501b, which may be advantageously used by the right in-ear utility device 505a and the left in-ear utility device 505b. Maintaining these cues by applying similar signal processing (e.g., the DSP 212 shown in FIG. 2A) on both the right in-ear utility device 505a and left in-ear utility device 505b help with sound localization of the speaker of interest, e.g., the user of the in-ear utility device. Therefore, results may be improved when the right in-ear utility device 505a communicates with the left in-ear utility device 505b (e.g., the right in-ear utility device 505a transfers external sounds to the left in-ear utility device 505b). With improved sound localization of the speaker of interest (e.g., the user of the in-ear utility device), speech understanding and communication may improve, according to an embodiment of the invention.

When the right in-ear sound device 505a communicates (e.g., transfers external sounds) with the left in-ear sound device, binaural beamforming can be conducted to narrow the directional focus of the beam so that anything outside that region is attenuated which improve the signal-to-noise ratio significantly and improves speech recognition, according to an embodiment of the invention. Embodiments of the invention that perform beamforming may include two microphones per in-ear utility device 505a, 505b, two microphones for the right in-ear utility device 505a and two microphones for the left in-ear utility device 505b, and the ports for the microphones may typically be located at some distance away from each other in the in-ear utility device 505a, 505b.

Moreover, once the source of the speech of interest is determined (e.g., the user of the in-ear sound device), the in-ear sound devices 505a, 505b can amplify the speech of interest and reduce the surrounding sound for further improvements in speech intelligibility.

The in-ear utility device 501 may communicate (e.g., via the communication module 204 shown in FIG. 2A) with a counterpart in-ear utility device (e.g., an in-ear utility device 501b in the left ear communicating with an in-ear utility device in the right ear 501a) to improve overall functionality. For example, the microphone(s) in the left ear in-ear utility device 501b may combine received sounds with the microphone(s) in the right ear in-ear utility device 501a. Inputs from these multiple microphones may improve overall noise cancellation for each in-ear utility device 501a, 501b.

Similarly, microphones in either or both of the in-ear utility devices 501a, 501b may be placed in different locations. Placing the microphones in different locations allows different sound signals to be received by the in-ear utility device 501, and these different signals may facilitate noise cancellation.

Using voice profiles (e.g., voice profiles 211 stored in the data storage component 209 shown in FIG. 2A), a processor in the in-ear utility device 501 (e.g., the processor 207 shown in FIG. 2A) can employ noise cancellation to identify a very specific sound in a haze of noise (e.g., picking a particular person out in a crowd). So, for example, assume a user of the in-ear utility device 501 attends a concert with his/her spouse. Assume further that the in-ear utility device 501 has a voice profile of the spouse. By applying the voice profile for the spouse (e.g., a voice profile 211 stored in the data storage component 209), the in-ear utility device's noise cancellation process can use the voice profile as a filter to cancel sounds not fitting the voice profile and thereby allow the user to hear the spouse's voice at a greater distance in a noisy crowd than would be the case without the additional processing or with the unaided ear.

Voice profiles could take a number of different formats but typically include information regarding the tonality, cadence, and frequency response of the person associated with the voice profile. Creating such profiles are not a part of the invention herein; however, such voice profiles can be created by having a person record a small number of sentences and then analyzing the response to derive the essential characteristics of the person's voice. Embodiments of the in-ear utility device 501 could obtain and store a large number of voice profiles (e.g., in the storage device 209 shown in FIG. 2A). Voice profiles are one representative embodiment of an audio profile, which could be a similar profile for some sound (human, animal, machine, etc.) that is amenable to being used as a filter; thus, the voice profiles discussed herein are representative examples of audio profiles.

The enhancement of a speaker's voice can be performed in a number of ways. For example, from a spectrogram of a speech, the pitch range, intonational pattern, voice quality, dialectal traits of the speaker can be obtained. In other words, the characteristics of the speaker's voice or voice biometrics can be gleaned.

If the data storage component of the in-ear utility device (e.g., the data storage component 209 shown in FIG. 2A) has a database of different people's voice profiles (e.g., based on voice biometrics), then the processor (e.g., the processor 207 shown in FIG. 2A) can identify a particular speaker in a speech sample. Once the speaker of interest is determined, then the incoming sound captured by the in-ear utility device 501 can be filtered by the characteristics of the speaker of interest and that received sound signal can be amplified under the direction of the processor and all other sounds can be filtered or diminished. Using statistical models of speech and noise, once the processor of in-ear utility device 501 knows the temporal and spectral characteristics of speech of interest, the processor can engage the filtering out of all other sounds.

FIG. 5C illustrates a portion of the distal ends of two in-ear utility devices 501*a*, 501*b* in a single user's ears 505*a*, 505*b* in a head 554, according to an embodiment of the invention. FIG. 5C shows the right ear 505 shown in FIG. 5B and adds a left ear 505*b*.

The distal ends of the in-ear utility devices 501*a*, 501*b* provide a fixed distance from the user's mouth 507 since the in-ear utility devices 501*a*, 501*b* are anchored in the user's ear canals. As previously shown in FIG. 1A and FIG. 1B and FIGS. 5A-5B, the in-ear utility devices 501*a*, 501*b* are placed in the user's ear canal (e.g., the ear canal 115 shown in FIG. 1A) during operation and are far less subject to movement once placed in the user's ears 505*a*, 505*b*.

Thus, the in-ear utility device 501 essentially resides at a fixed distance from the user's mouth 507. The fixed proximity to the user's mouth 507 coupled with the stability of the fixed distance simplifies calibration of the user's voice by the processor (e.g., the processor 207 shown in FIG. 2A) and simplifies recognition of the user's voice.

Sounds from the user's mouth 507 can be focused and amplified by allowing the in-ear utility devices 501*a*, 501*b* to advantageously apply the natural focusing and amplification by the pinna 513*a*, 513*b* of the user's ears 505*a*, 505*b*, as shown in FIG. 5B, especially the conchae bowl portion of the pinna. Here, sounds from the user's voice 520*a*-1, 520*b*-1, 520*c*-1 traveling to the user's right ear 505*a* can be collected and focused naturally by the pinna 513*a* in the user's right ear 505*a* before entering a microphone port on the in-ear utility device 501*a*. Similarly, sounds from the user's voice 520*a*-2, 520*b*-2, and 520*c*-2 traveling to the user's left ear 505*b* can be collected and focused naturally by the pinna 513*b* in the user's left ear 505*b* before entering a microphone port on the in-ear utility device 501*b*.

Figure 5D:
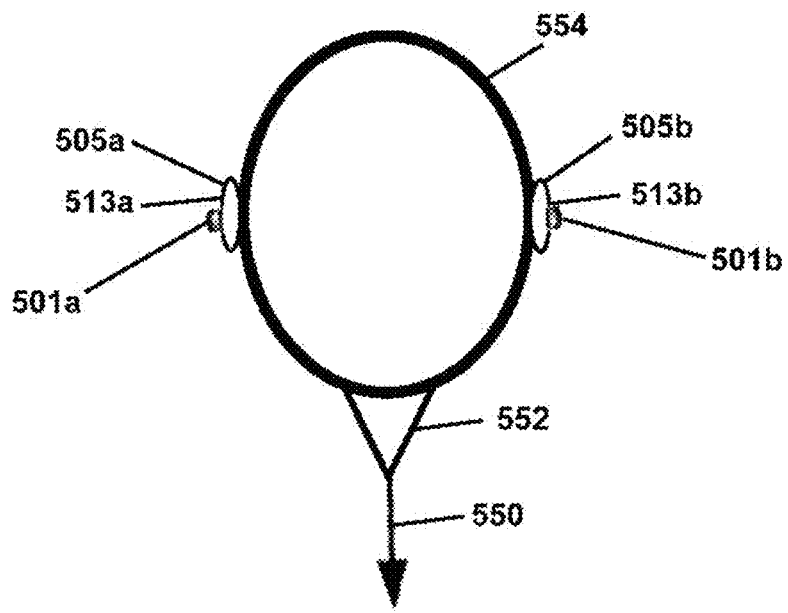
FIG. 5D illustrates a top-down view of in-ear sound devices 505*a*, 505*b* performing binaural beamforming for sounds in front of the head 554 shown in FIG. 5C, according to an embodiment of the invention.

FIG. 5D illustrates a top-down view of in-ear sound devices 505*a*, 505*b* performing binaural beamforming for sounds in front of the head 554 shown in FIG. 5C, according to an embodiment of the invention. When the in-ear sound devices 505*a*, 505*b* perform binaural beamforming, then the in-ear sound devices 505*a*, 505*b* will particularly focus on sounds in front of the user's head 554 and will in particular focus on sounds 550 essentially pointed to by the user's nose 552.

The in-ear sound device 505*a* and the in-ear sound device 505*b* may be paired with each other, according to an embodiment of the invention. One of the in-ear sound devices may serve as a master device while the other device serves as a slave device. Microphone inputs from the in-ear sound devices 505*a*, 505*b* can be combined (e.g., in the master in-ear sound device) so that signal processing (e.g., using DSP 212 shown in FIG. 2A) can be performed on the microphone inputs so as to pick out a specific object (e.g., a person) that the user wants to concentrate on (e.g., via beamforming) and/or to improve signal-to-noise ratio in the combined signal, according to an embodiment of the invention.

When the right in-ear sound device 505*a* communicates its sound inputs with the left in-ear sound device 505*b*, binaural beamforming can be conducted to narrow the directional focus of the beam so that anything outside a region in an arc around the front of the user's head is attenuated, which improves the signal-to-noise ratio significantly and improves speech recognition, according to an embodiment of the invention.

Embodiments of the invention that perform beamforming may include at least two microphones per in-ear utility device 505*a*, 505*b*, e.g., two microphones for the right in-ear utility device 505*a* and two microphones for the left in-ear utility device 505*b*.

The ports for the microphones may typically be located at some distance away from each other in the in-ear utility device 505*a*, 505*b*. For example, the microphone port for ambient sound may be located on the opposite side of the in-ear utility device from the voice focused port, such as the voice focused port 512 shown in FIG. 5A. In other words, in some embodiments of the invention, an outwardly facing ambient noise port (such as the ambient noise ports 514) might be replaced (or supplemented) by an ambient noise port at a location opposed to the voice focused port.

In some embodiments, it may be simpler to have two ambient noise ports (e.g., one outwardly facing and one opposed to the voice focused port) and two ambient noise microphones with a controller (e.g., the processor 207 shown in FIG. 2A) that simply switches one ambient microphone off and another on, depending on whether the in-ear utility device is performing binaural beamforming or a similar function as opposed to performing a task optimized by an outwardly facing ambient microphone port. Of course, it would also be possible to use a smaller number of microphones and have some sort of physical device that opened and closed the various input ports depending upon their function.

Figure 5E:
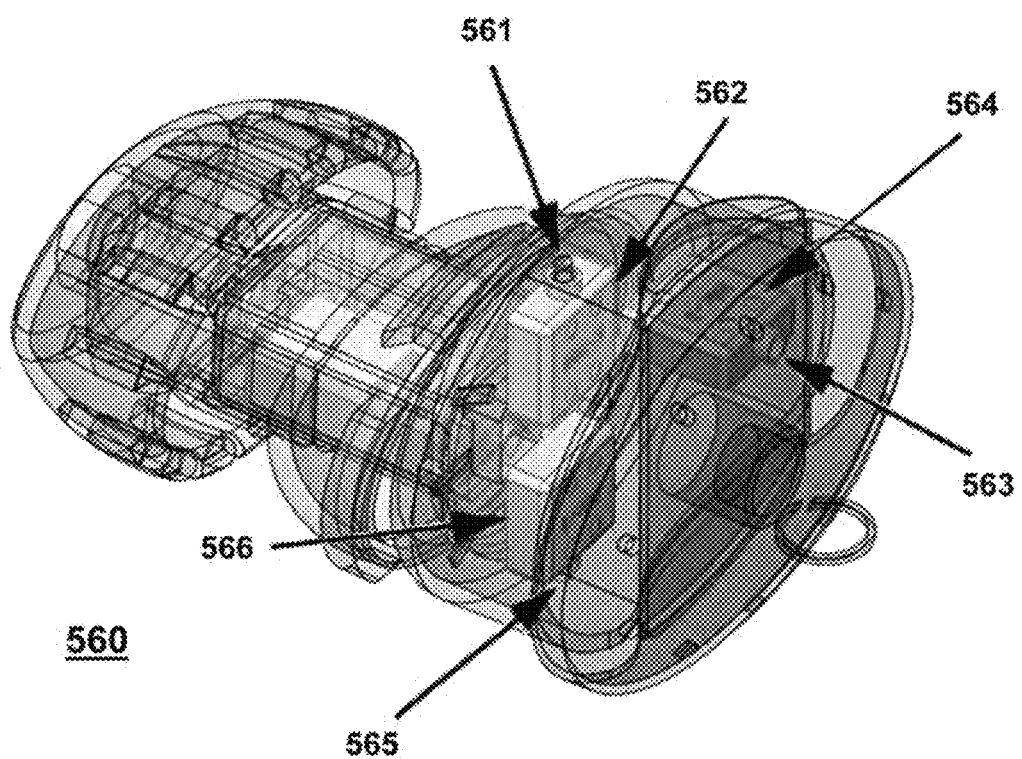
FIG. 5E illustrates an in-ear utility device 560 having two ambient noise microphones 562, 564 and two ambient noise microphone ports 561, 563 along with a voice focused microphone 566 and a voice focused microphone port 565, according to an embodiment of the invention.

FIG. 5E illustrates an in-ear utility device 560 having two ambient noise microphones 562, 564 and two ambient noise microphone ports 561, 563 along with a voice focused microphone 566 and a voice focused microphone port 565, according to an embodiment of the invention. The ambient noise port 561 is on the opposite side of the in-ear utility device 560 from the voice focused microphone port 565. The ambient noise port 563 can take a number of forms and shapes, including those shown in FIG. 5A and FIG. 5F, and need not be a single port but could be an array of ports as well.

The voice-focused microphone port 565 may typically come to rest inside the user's ear canal 515 at a portion facing the user's mouth 507 and in a region to benefit from natural amplification provided by the pinna 513 of the user's ear 505, according to an embodiment of the invention. The ambient noise port 561 may typically come to rest inside the user's ear canal 515 at a portion facing away from the user's mouth 507 and in a region to benefit from natural amplification provided by the pinna 513 of the user's ear 505, according to an embodiment of the invention. Instructions for proper placement of the in-ear sound device 560 may be provided to the user via various instructional materials. In addition, the accelerometer sensor 206*a* may be configured to determine the orientation of the ambient noise port 561 and the voice-focused microphone port 565. For example, the accelerometer sensor 206*a*, working with the processor and the speaker (e.g., the processor 207 and the speaker 208 shown in FIG. 2A), could signal a beeping sound when the in-ear sound device has an acceptable orientation, according to an embodiment of the invention.

A control circuit or processor (such as the processor 207 shown in FIG. 2A) controls which microphones 562, 564, 566 are operating at any given time, e.g., by turning off the power to these microphones. When the power to a given microphone is turned off, then sounds entering through the microphone's respective port will be not be amplified and essentially ignored.

For example, the processor switches on microphones 562, 566 when the in-ear utility device 560 is performing a beamforming function, and the microphone 564 is similarly switched off for this task. Similarly, the processor may switch off microphones 562, 566 and switch on microphone 564 if the in-ear utility device is focused on an ambient noise listening task. Likewise, microphones 562, 564 may be switched off, and microphone 566 turned on when the in-ear utility device 560 is focused on a voice recognition task, according to an embodiment of the invention. The processor may also switch on microphones 564, 566 for certain listening tasks, according to an embodiment of the invention. As discussed above, when one of the microphones 562, 564, 566 is switched off, then sounds entering a respective port 561, 563, 565 are not processed and essentially ignored.

The processor may turn microphones on and off fairly rapidly, allowing the in-ear utility device 560 to perform a number of functions and tasks nearly concurrently, according to an embodiment of the invention. In addition, as discussed herein, these various hearing tasks may be controlled by the user via various voice commands received by the in-ear utility device, according to an embodiment of the invention.

Figure 5F:
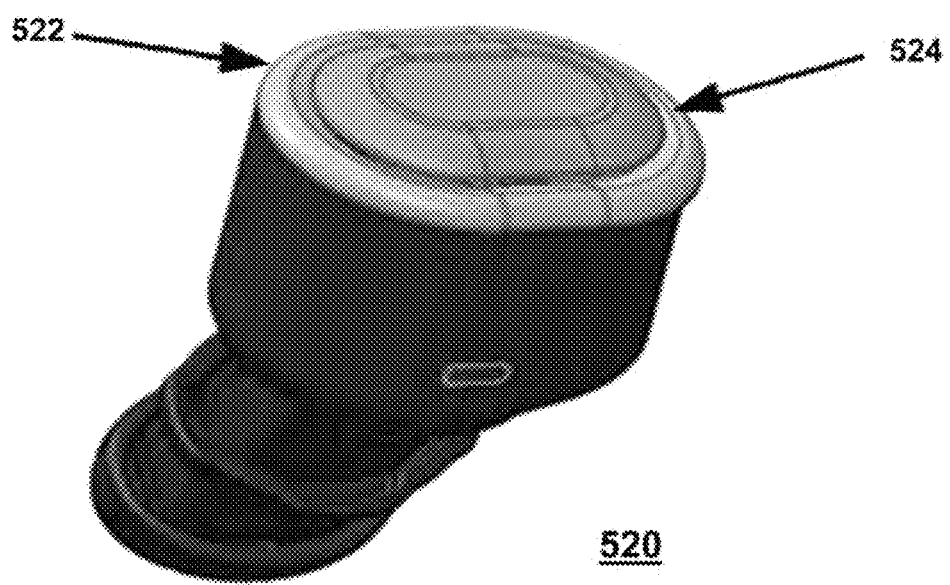
FIGS. 5F-5H illustrate a 360-degree slit port 524 for the microphone port on a distal end 522 of an in-ear utility device 520, according to an alternative embodiment of embodiment of the invention.
Figure 5G:
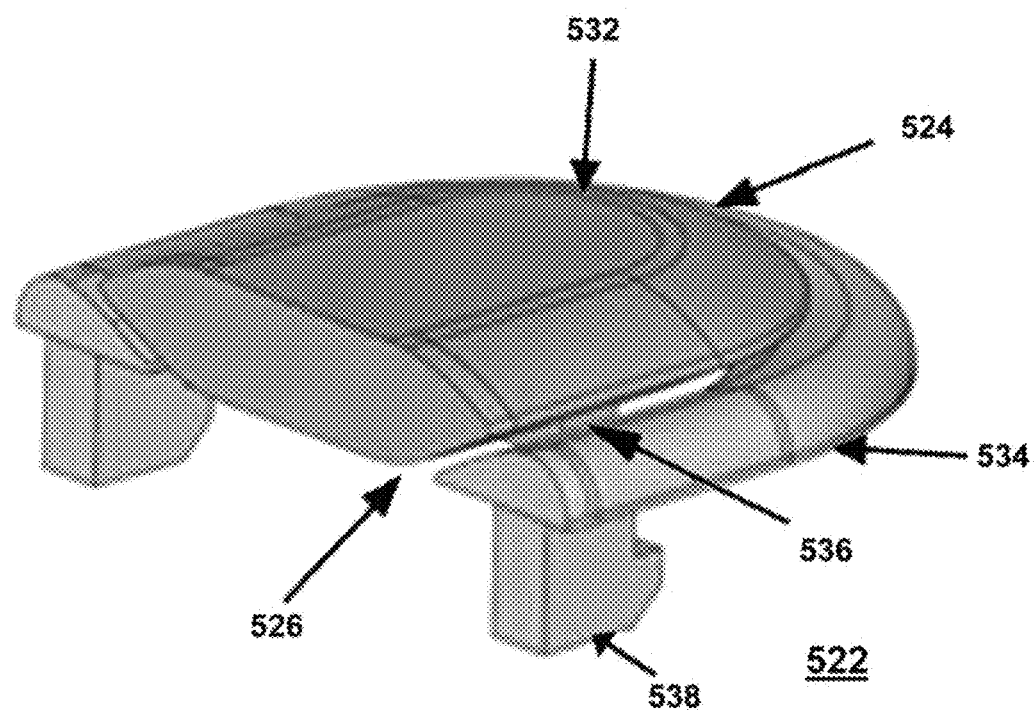
Figure 5H:
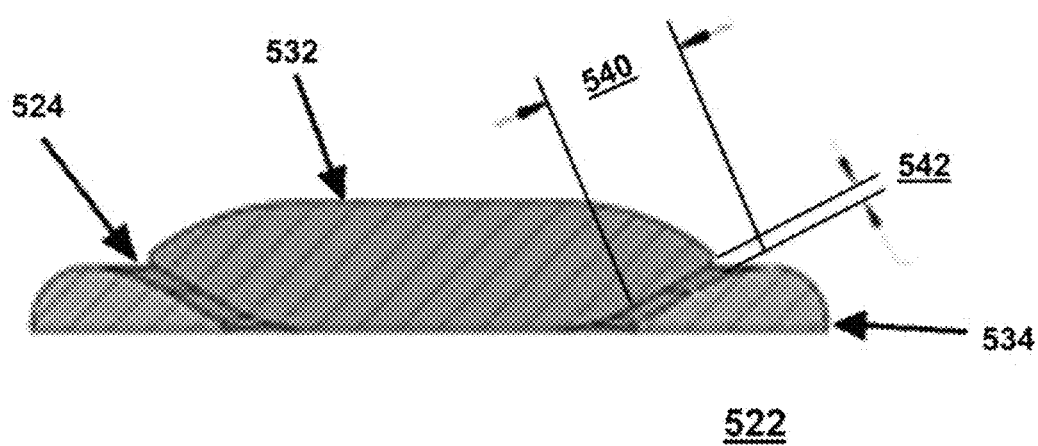

FIGS. 5F-5H illustrate a 360-degree slit port 524 for the microphone port on a distal end 522 of an in-ear utility device 520, according to an alternative embodiment of embodiment of the invention. The slit port 524 provides an opening all around the distal end 522 and directs sounds to a microphone (e.g., the first microphone 414 shown in FIG. 4).

FIG. 5G illustrates a cross-section 526 of the distal end 522 of the in-ear utility device 520 showing the slit port 524, according to an embodiment of the invention. A top portion 532 of the slit port 524 is suspended slightly above a bottom portion 534. The top portion 532 can be fastened to the bottom portion 534 by a variety of fasteners 536. The fastener 536 could be a hook, a hinge, a tongue that is glued to connect the top portion 534 to the bottom portion 536, a piece that is melted, or even formed as an integral piece, etc.

The bottom portion 534 can be attached to the body of the in-ear utility device 520 by a number mechanisms, such as a hook 538 that slides into another piece on the in-ear utility device 520, according to an embodiment of the invention.

FIG. 5H illustrates dimensions of the 360-degree slit port 524 on the distal end 522 of the in-ear utility device 520, according to an embodiment of the invention. A top portion 532 may have a smaller diameter in comparison to the inner diameter of the bottom portion 534 such that the two pieces are separated by a distance 540. The distance 540 may range from 1.0 to 2.7 millimeters, according to an embodiment of the invention. The top portion 532 may be raised above the bottom portion 534 by a distance 542. The distance 542 may range from 0.1 to 0.5 millimeters, according to an embodiment of the invention.

Figure 6A:
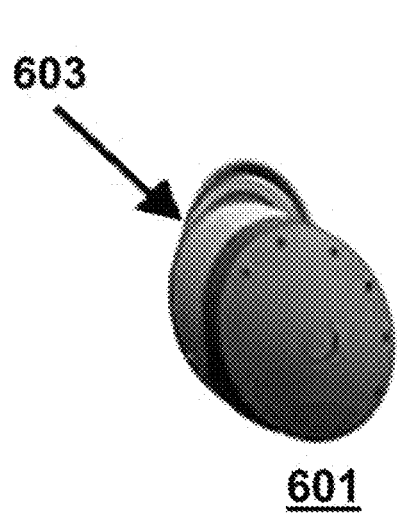
FIGS. 6A-6C illustrate a swivel joint 603 in the in-ear utility device 601 that allows the in-ear utility device 601 to pivot from zero (vertical) to negative 30 degrees from zero to plus 30 degrees.
Figure 6B:
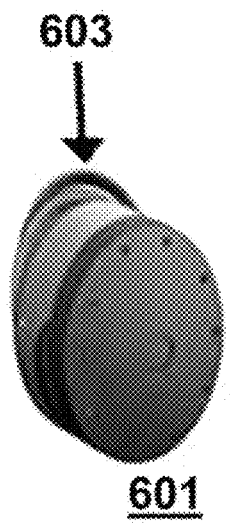
Figure 6C:
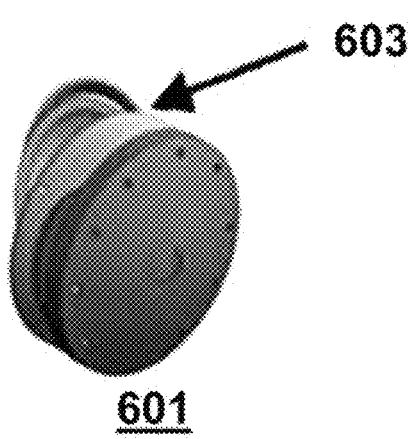

FIGS. 6A-6C illustrate a swivel joint 603 in the in-ear utility device 601 that allows the in-ear utility device 601 to pivot from zero (vertical) to negative 30 degrees and from zero to plus 30 degrees. The swivel joint 603 may pivot to other ranges of degrees in other embodiments of the invention.

Human ears often have ear canals (e.g., the ear canal 115 shown in FIG. 1) of various shapes and sizes (e.g., an s-shaped ear canal). Thus, the swivel joint 603 facilitates placing the in-ear utility device 601 in the user's ear securely.

FIG. 6A shows the in-ear utility device in a −30 degree position. FIG. 6B shows the in-ear utility device 601 in a zero position, and FIG. 6C shows the in-ear utility device 601 in a +30 degree position, according to an embodiment of the invention.

The swivel joint 603 allows the in-ear utility device 601 to pivot into an ear canal (e.g., the ear canal 115 shown in FIG. 1A) that is twisted and not straight, according to an embodiment of the invention. Embodiments of the in-ear utility device could pivot to a greater and/or smaller degree, e.g., from 10 degrees to 90 degrees.

Some users of the in-ear utility device 601 may have ear canals that are not straight but spiral upwards or downwards or both. The in-ear utility device 601 having the swivel joint 603 may be useful to users having straight ear canals but will be especially useful for user's having spiral ear canals.

The swivel joint 603 allows the in-ear utility device 601 to move closer to the user's eardrum (e.g., the eardrum 104 shown in FIG. 1A). The closer the in-ear utility device 601 resides to the user's eardrum 104, the smaller amounts of power the in-ear utility device 601 needs to operate the speaker (e.g., the speaker 108), according to an embodiment of the invention. In addition, the closer proximity of the in-ear utility device 601 to the user's eardrum may also increase the quality of sound delivered by the in-ear utility device 601.

The in-ear utility device 601 may have more than one swivel joint 603. Additional swivels placed in the in-ear utility device 601 will increase the degrees of freedom offered by the in-ear utility device 601. It is known in the art, that some users have ear canals that are so spiraling that they double back on themselves. Such users will particularly benefit from the increased degrees of freedom provided by the swivel(s) in the in-ear utility device, according to an embodiment of the invention.

Figure 7:
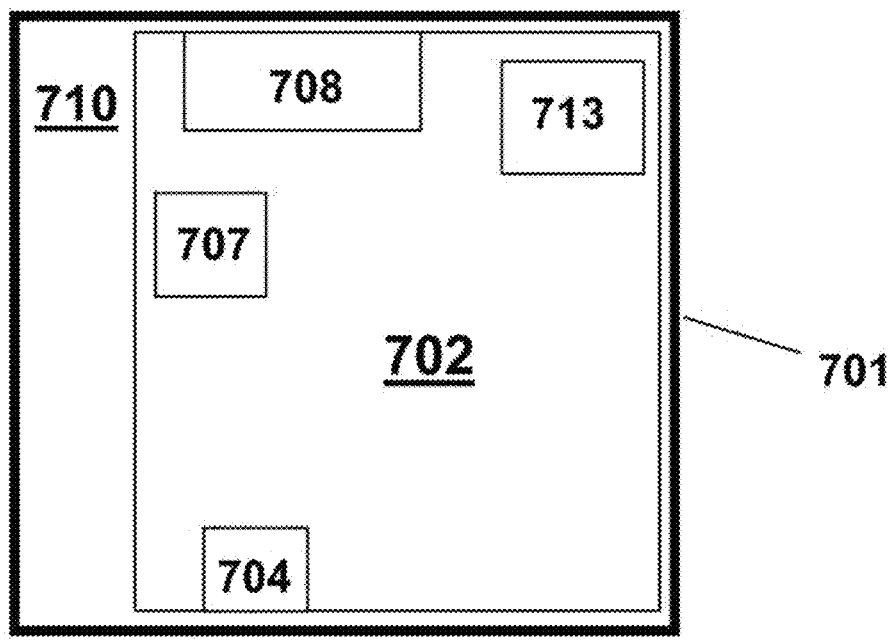
FIG. 7 illustrates an embodiment of an in-ear utility device 701 configured to function as a headphone, according to an embodiment of the invention.

FIG. 7 illustrates an embodiment of an in-ear utility device 701 configured to function as a headphone, according to an embodiment of the invention. The in-ear utility device 701 may have the shape and other ergonomic characteristics of the in-ear utility device 303 shown in FIG. 3, for example.

The in-ear utility device 701 comprises a speaker 708, a battery 713, a communication module 704, and a control circuit 707 in an electronic component package 702. The in-ear utility device 701 may comprise additional electronic components in the headphone embodiment. However, the components provided here are sufficient to enable an in-ear headphone capability. The electronic component package 702 is placed in or on a body 710 designed for comfortably wearing for long periods of time, according to an embodiment of the invention. The electronic component package 702 does not need to be inserted as a single unit; individual components may be inserted individually, for example.

The control circuit 707 may operate in a conventional manner for such circuits, controlling the receipt of data (e.g., music or voice data) from outside the in-ear utility device 701 via the communication module 704 and directing transfer of the data to the speaker 708, with operations powered by the battery 713. The control circuit 707 may in some embodiments comprise a dedicated computer chip (e.g., the processor 207 shown in FIG. 2A) configured to provide equivalent or superior functionality to a control circuit, according to an embodiment of the invention.

Figure 8:
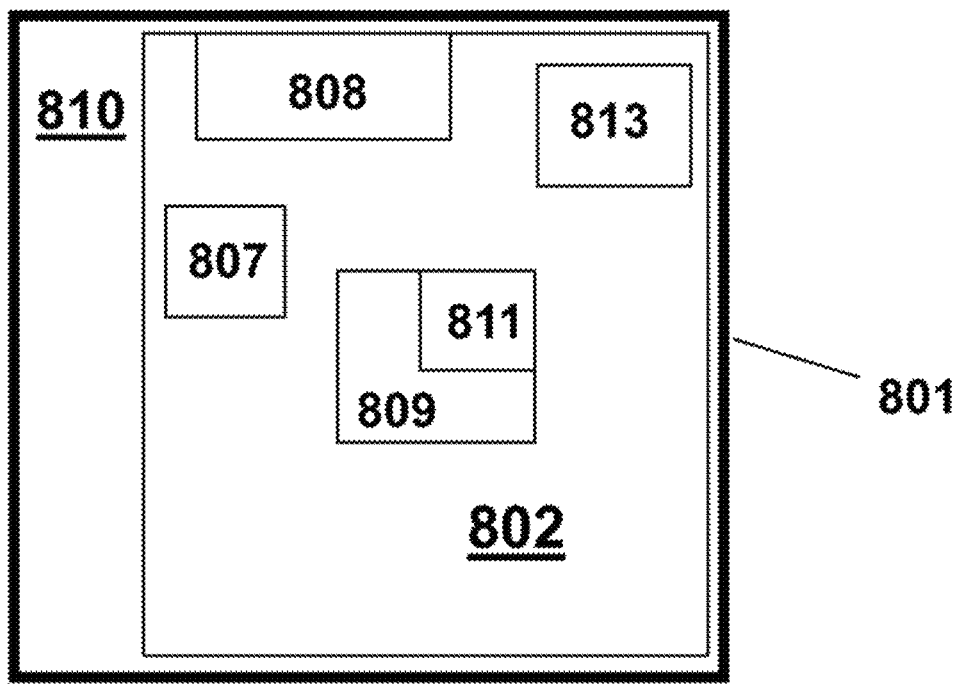
FIG. 8 illustrates an embodiment of an in-ear utility device 801 configured to function as a music player, according to an embodiment of the invention.

FIG. 8 illustrates an embodiment of an in-ear utility device 801 configured to function as a music player, according to an embodiment of the invention. The in-ear utility device 801 may have the shape and other ergonomic characteristics of the in-ear utility device 303 shown in FIG. 3, for example.

The in-ear utility device 801 comprises a speaker 808, a battery 813, a data storage component 809, and a control circuit 807 in an electronic component package 802. The in-ear utility device 801 may comprise additional electronic components in the music player embodiment. However, the components provided here are sufficient to provide a music player capability. The data storage component 809 includes music data 811. The electronic component package 802 is placed in or on a body 810. The electronic component package 802 does not need to be inserted as a single unit; individual components may be inserted individually, for example.

The control circuit 807 may operate in a conventional manner for such circuits, obtaining music data 811 from the data storage component 809 and directing transfer of the music data 811 to the speaker 808, with operations powered by the battery 813. The control circuit 807 may in some embodiments comprise a dedicated computer chip (or processor) configured to provide equivalent or superior functionality to a control circuit, according to an embodiment of the invention. The in-ear utility device 801 may include a communications module, such as the communications module 204 shown in FIG. 2A. The communications module may provide a means for storing new music. Alternatively, a port could allow music to be directly added to the data storage component 809.

Figure 9:
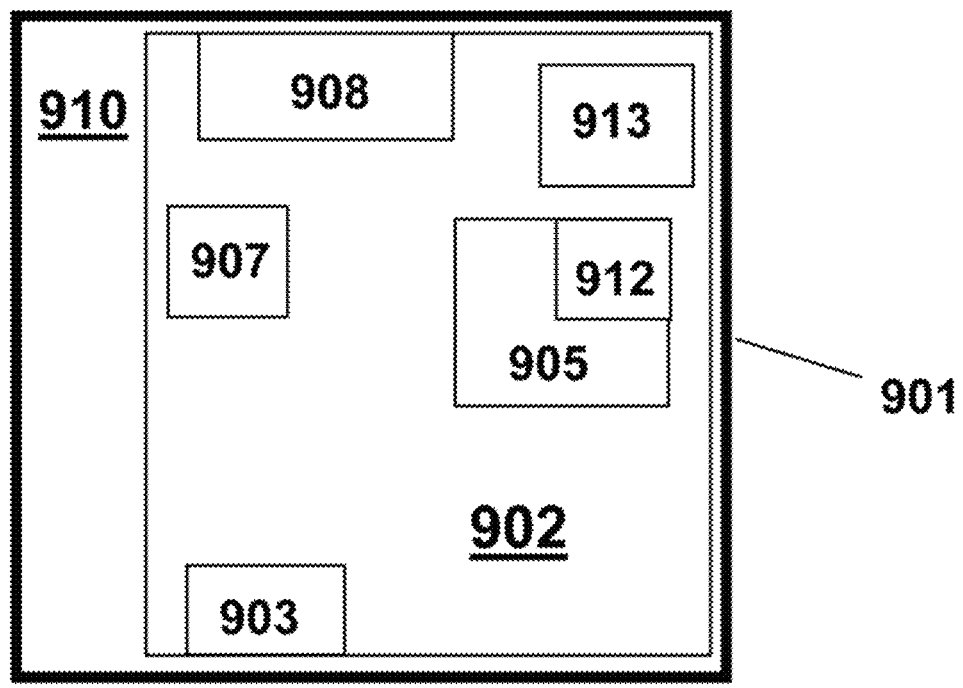
FIG. 9 illustrates an embodiment of an in-ear utility device 901 configured to provide hearing amplification, according to an embodiment of the invention.

FIG. 9 illustrates an embodiment of an in-ear utility device 901 configured to provide hearing amplification, according to an embodiment of the invention. The in-ear utility device 901 may have the shape and other ergonomic characteristics of the in-ear utility device 303 shown in FIG. 3 for example.

The in-ear utility device 901 comprises a speaker 908, a battery 913, a microphone 903, an amplifier 905, and a control circuit 907 in an electronic component package 902. The in-ear utility device 901 may comprise additional electronic components in the hearing amplification embodiment, such as a digital signal processor (DSP) 912. However, the components provided here are sufficient to provide an in-ear hearing amplification capability. The electronic component package 902 is placed in or on a body 910 design for comfortably wearing for long periods of time, according to an embodiment of the invention. The electronic component package 902 does not need to be inserted as a single unit; individual components may be inserted individually, for example.

The control circuit 907 may operate in a conventional manner for such circuits, receiving sound data from the microphone 903, directing transfer of the data to the amplifier 905 (and possibly the DSP 912), and then directing the amplified and/or enhanced sound to the speaker 908, with operations powered by the battery 913. The control circuit 907 may in some embodiments comprise a dedicated computer chip (or processor) configured to provide equivalent or superior functionality to a control circuit, according to an embodiment of the invention. In some embodiments, the control circuit 907 may also direct the operations of the DSP 912.

The in-ear utility device 901 may include additional microphones, as discussed above, and the microphones may have specialized ports depending upon their specific function, as discussed above. Embodiments of the in-ear utility device 901 may also include a voice recognition chip along the lines of the voice recognition chip previously discussed.

FIG. 10 illustrates an embodiment of an in-ear utility device 1001 configured to provide a walkie-talkie function (a portable, two-way radio transceiver), according to an embodiment of the invention. The in-ear utility device 1001 may have the shape and ergonomic characteristics of the in-ear utility device 303 shown in FIG. 3, for example.

The in-ear utility device 1001 comprises a speaker 1008, a battery 1013, a microphone 1003, a communication module 1004, and a control circuit 1007 in an electronic component package 1002. The in-ear utility device 1001 may comprise additional electronic components in the walkie-talkie embodiment. However, the components provided here are sufficient to provide an in-ear walkie-talkie capability. The electronic component package 1002 is placed in or on a body 1010 designed for comfortably wearing for long periods of time, according to an embodiment of the invention. The electronic component package 1002 does not need to be inserted as a single unit; individual components may be inserted individually, for example.

The control circuit 1007 may operate in a conventional manner for such circuits, receiving sound data from the microphone 1003, directing transfer of the data to the speaker 1008, with operations powered by the battery 1013. The control circuit 1007 may also send the audio data received by the microphone 1003 to a remote device using the communications module 1004. The control circuit 1007 may also receive audio data from the communication module 1004 and direct the audio data to the speaker 1008.

The control circuit 1007 may in some embodiments comprise a dedicated computer chip (or processor like the processor 207 shown in FIG. 2A) configured to provide equivalent or superior functionality to a control circuit, according to an embodiment of the invention.

FIG. 11 illustrates an embodiment of an in-ear utility device 1101 configured in a single, integrated body 1118 rather than as a multi-pieced body as shown and described in FIG. 3-5. The integrated body 1118 of the in-ear utility device 1101 includes a microelectronics component package 1113. The in-ear utility device 1101 is shown in FIG. 11 with the body 1118 separated from a seal 1102 that typically covers at least a tip end of the body 1118 when the in-ear utility device 1101 is inserted into the user's ear canal (e.g., the ear canal 115 shown in FIG. 1A).

Embodiments of the in-ear utility device 1101 may fit completely inside the user's ear canal (e.g., the ear canal 115 shown in FIG. 1A) with no part of the device extending outside the user's ear. The in-ear utility device 1101 may include a ring 1111 that facilitates removal of the device from the user's ear, e.g., the in-ear utility device 1101 may be removed by latching the ring 1111 with a small utility device having a matching hook. In an alternative embodiment, the body 1118 may be made of a metallic substance such that the in-ear utility device 1101 can be removed from the user's ear using a magnet.

Embodiments of the invention provide an in-ear utility device 1101 covered, or partially covered, with a seal 1102 that is comfortable to wear for a long period of time. The seal 1102 can be produced in bulk eliminating the need for customizing the body 1118 of the in-ear utility device 1101. The external seal 1102 deforms when the in-ear utility device 1101 is inserted into a user's ear canal (e.g., the ear canal 115 shown in FIG. 1A) without damaging the in-ear utility device 1101 or causing harm to the user's ear (e.g., the ear 105 shown in FIG. 1A).

The deformable seal 1102 cushions the user's ear canal (e.g., the ear canal 115 shown in FIG. 1A) from the material of the in-ear utility device's body 1118, allowing the user to wear the in-ear utility device 1101 for an extended period of time. The seal 1102 allows the body 1118 of the in-ear utility device 1101 to be a "one size fits all" and conform to a broad range of ear canal anatomies, according to an embodiment of the invention. The seal 1102 may be produced in several sizes (e.g., small, medium, larger) to accommodate differences in the size of human ear canals (e.g., the ear canal 115 shown in FIG. 1A).

The electronic component package 1113 is embedded in the body 1118 of the in-ear utility device 1101 and includes electronic circuitry allowing the in-ear utility device 1101 to be inserted into the user's ear canal (e.g., the ear canal 115 shown in FIG. 1A) without damaging the in-ear utility device 1101 or causing injury to the user's ear, according to an embodiment of the invention.

The electronic component package 1113 may include a speaker 1109 disposed at the proximal tip 1108 (e.g., the proximal tip 107 shown in FIG. 1A) of the in-ear utility device 1101. The speaker 1109 is disposed at the proximal tip of the body 1118, and when the seal 1102 is fitted onto the in-ear utility device 1101, the proximal tip 1108 for the in-ear utility device 1101 becomes the seal 1102, according to an embodiment of the invention.

Embodiments of the in-ear utility device 1101 have no wires protruding from the body 1118 and no external behind-the-ear components associated with the in-ear utility device 1101. The in-ear utility device 1101 may be used by the hearing impaired population as well as the general public. Thus, the in-ear utility device 1101 may be used for sound amplification and communication purposes as well as a number of additional purposes, such as those previously discussed herein.

The in-ear utility device 1101 may also include a microphone port (e.g., the microphone port 512 shown in FIG. 5) to facilitate receipt of sounds into the in-ear utility device 1101, according to an embodiment of the invention. The in-ear utility device 1101 may have other ports, including ports for specific purposes, such as voice receipt/recognition and ambient noise receipt.

In-Ear Utility Device Recharging Case

FIGS. 12A-12D illustrate a recharging case 1200 configured to recharge a pair of in-ear utility devices 1201, 1202, according to an embodiment of the invention.

Figure 12A:
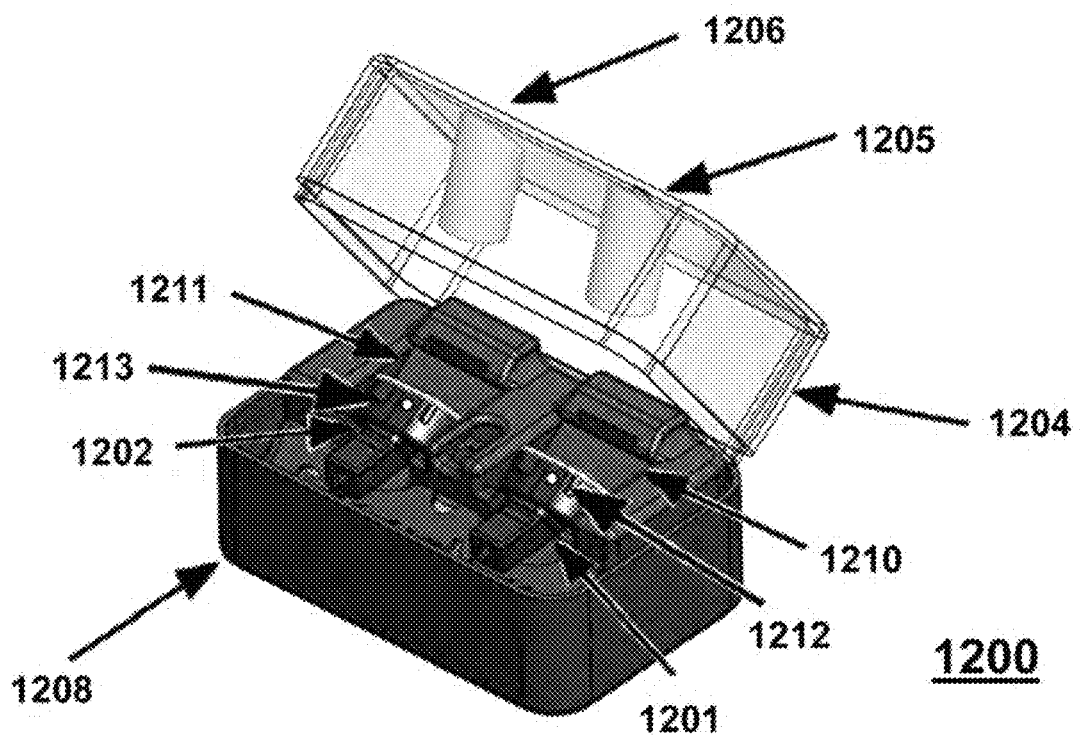
FIGS. 12A-12D illustrate a recharging case 1200 configured to recharge a pair of in-ear utility devices 1201, 1202, according to an embodiment of the invention.

FIG. 12A illustrates a pair of in-ear utility devices 1201, 1202 inserted into charging ports 1210, 1211 in the bottom 1208 of the charging case 1200. The lid 1204 includes two magnets 1205, 1206, according to an embodiment of the invention. The magnets 1205, 1206 are mounted in the lid 1204 in alignment with the charging ports 1210, 1211. Thus, the magnets 1205, 1206 will be above the in-ear utility devices 1201, 1202 when the in-ear utility devices 1201, 1202 are in the charging ports 1210, 1211, according to an embodiment of the invention.

When a lid 1204 is open, the magnetic field from the magnets 1205, 1206 will not engage the Hall Effect sensors in the in-ear utility devices, e.g., the Hall Effect sensor 219 shown in FIG. 2A.

Figure 12B:
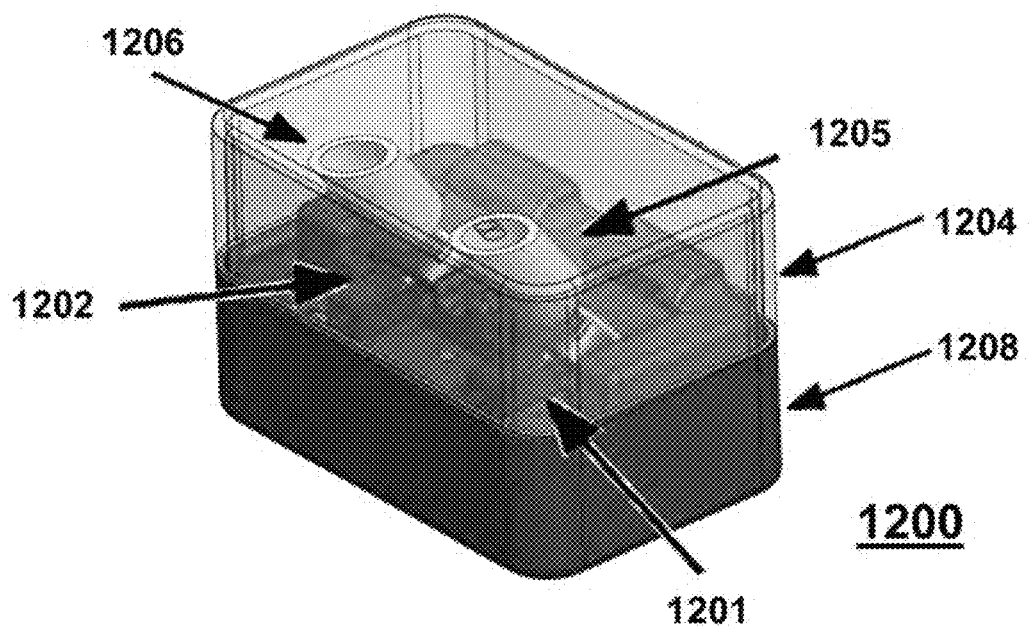

As shown in FIG. 12B, when the lid 1204 is shut, the magnets 1205, 1206 trigger the Hall Effect sensors in the in-ear utility devices 1201, 1202. As discussed with the Hall Effect sensor 219 shown in FIG. 2A, the Hall Effect sensors engage the turning off of the in-ear utility devices 1201, 1202.

The in-ear utility devices 1201, 1202 may include LEDs 1212, 1213, according to an embodiment of the invention. When the user opens the lid 1204 after the in-ear utility devices 1201, 1202 have re-charged, the Hall Effect sensor (e.g., the Hall Effect sensor 219 shown in FIG. 2A) will engage the turning on of the in-ear utility devices 1201, 1202. Turning on the in-ear utility devices 1201, 1202 will also cause the LEDs 1212, 1213 to turn on. The LEDs 1212, 1213 will flash until the in-ear utility device 1201 has been paired with the in-ear utility device 1202, according to an embodiment of the invention. Once the in-ear utility devices 1201, 1202 have been paired with each other, then the LEDs 1212, 1213 will stop flashing.

The in-ear utility devices 1201, 1202 may be paired with each other using a third device (e.g., a smartphone), according to an embodiment of the invention. The in-ear utility devices 1201, 1202 may also be paired with each other using a pairing circuit included in the charging case 1200, according to an embodiment of the invention.

Figure 12C:
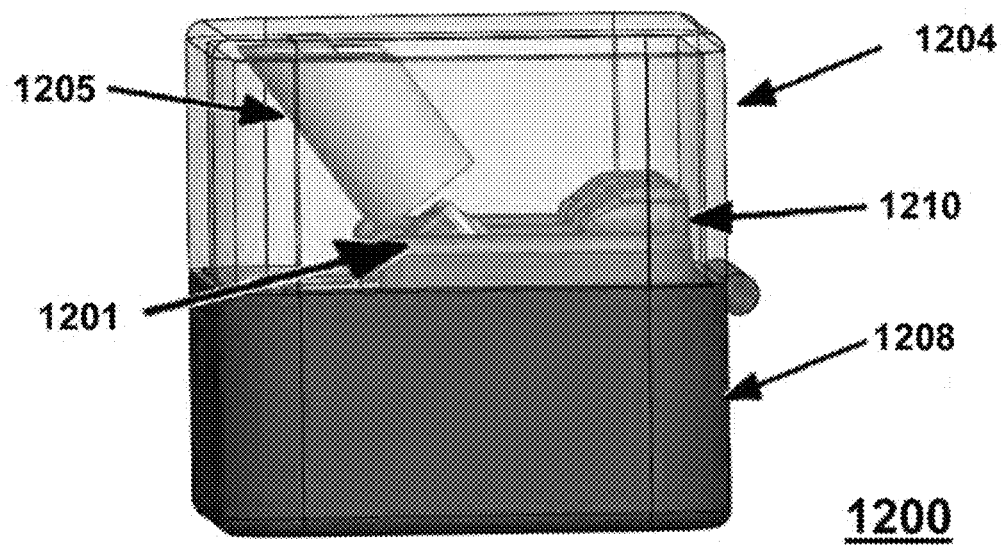

FIG. 12C provides a side view of the charging case 1200 with the lid 1204 closed while the in-ear utility device 1201 charges in the charging port 1210, according to an embodiment of the invention.

The magnetic field produced by the magnet 1205 should be perpendicular to the Hall Effect sensor (e.g., the Hall Effect sensor 219 shown in FIG. 2A) in the in-ear utility device 1201 in order for the magnet 1205 to activate the Hall Effect sensor. Thus, the magnet 1205 and the charging port 1210 should be positioned inside the charging case 1200 such that the Hall Effect sensor in the in-ear utility device 1201 is perpendicular to the magnet 1205, according to an embodiment of the invention. As discussed above, when the lid 1204 is closed, the magnetic field activates the Hall Effect sensor, causing the in-ear utility device 1201 to turn off, and the LED 1212 (not shown in FIG. 12C will also not flash.

Figure 12D:
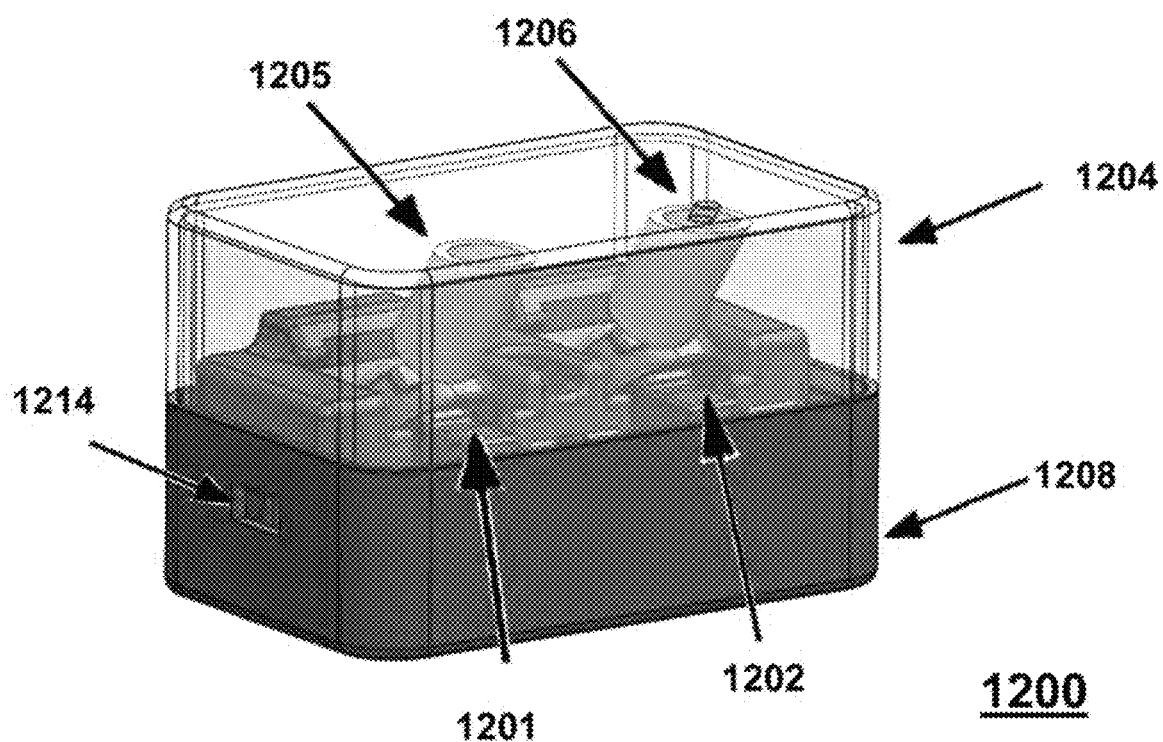

FIG. 12D illustrates a micro-USB port 1214 that can provide power to the charging case 1200, according to an embodiment of the invention. Once the in-ear utility devices 1201, 1202 are changed, the user can unplug the charging case 1200 and take the case 1200 with him/her. Depending on the battery type in the in-ear utility devices 1201, 1202, the in-ear utility devices 1201, 1202 will be able to retain their charge for some period of time in the case 1200 after being recharged, according to an embodiment of the invention.

Figure 13:
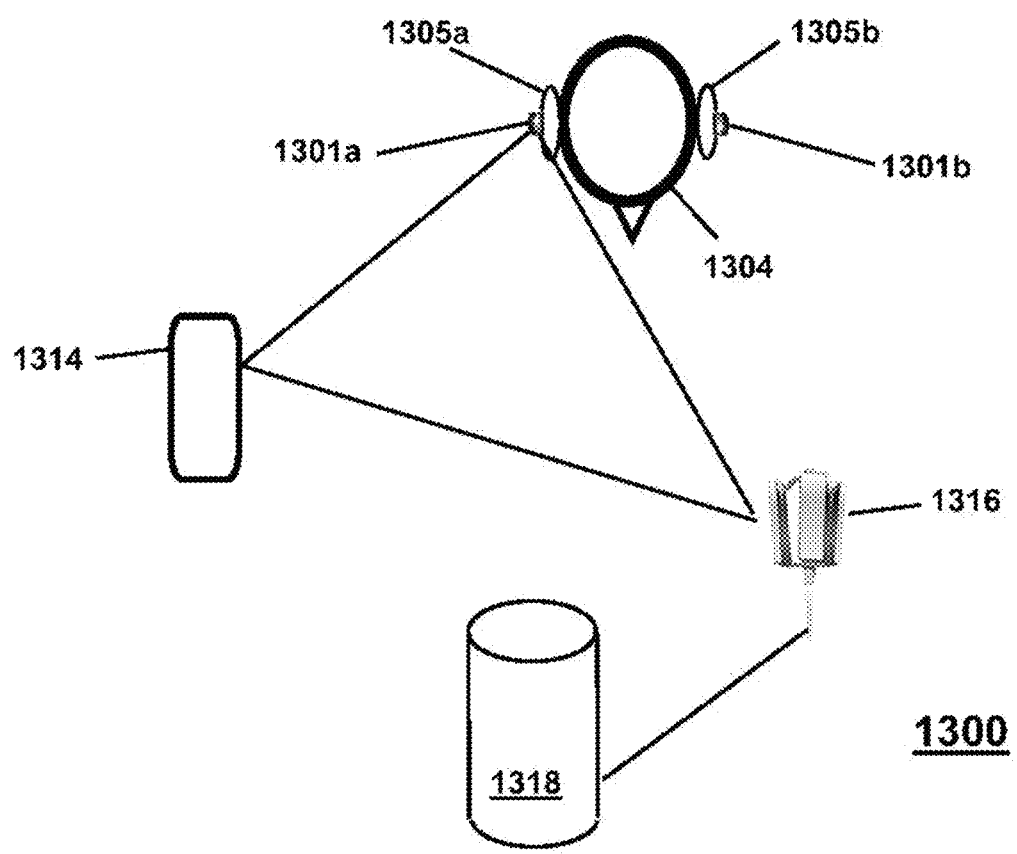
FIG. 13 illustrates a network 1300 through which various processing tasks for in-ear utility devices 1301*a*, 1301*b* can be distributed, according to an embodiment of the invention.

FIG. 13 illustrates a network 1300 through which various processing tasks for in-ear utility devices 1301a, 1301b can be distributed, according to an embodiment of the invention. Some processing tasks can be performed by the processors on the in-ear utility devices 1301a, 1301b; other processing tasks can be performed by a remote device, such as a smartphone 1314, and other processing tasks can be performed by a powerful remote computing facility 1318 (e.g., a cloud computing network), according to an embodiment of the invention.

A user may wear in-ear utility devices 1301a, 1301b in each ear 1305a, 1305b. In some configurations, one of the in-ear utility devices (e.g., the in-ear utility device 1301a) may serve as a master device between the two in-ear utility devices 1301a, 1301b, according to an embodiment of the invention. In other embodiments, each in-ear utility device may operate independently and communicate independently with remote devices, such as the smartphone 1314, and the remote computing facility 1318.

The processor (e.g., the processor 207 shown in FIG. 2A) in an in-ear utility device (e.g., the in-ear utility device 1301a) may be programmed to have an understanding of tasks that it can complete itself and tasks that should be completed by a remote device. So, for example, if the user asks the in-ear utility device 1301a, "Where is the nearest restaurant?" the processor on the in-ear utility device 1301a may recognize the utterance as an instruction. However, the processor may also recognize that this is a command that it cannot process alone.

Consequently, the processor passes the command to either the smartphone 1314 and/or the remote computing facility 1318, according to an embodiment of the invention. The remote computing facility 1318 may locate the requested information and return the answer to the in-ear utility device, which then delivers the answer to the speaker of the in-ear utility device. As previously discussed, the in-ear utility device may communicate to the smartphone 1314 using a protocol such as Bluetooth and may communicate to the remote computing facility 1318, possibly via a mobile base station 1316, according to an embodiment of the invention. The in-ear utility device 1301a may communicate to the mobile base station 1316 using a protocol such as GSM, according to an embodiment of the invention.

Any number of tasks may be performed on the in-ear utility device 1301a, and any number of tasks may be performed on the smartphone 1314 and/or the remote computing facility 1318, according to an embodiment of the invention. Tasks that may be most amenable to execution on the smartphone 1314 and/or the remote computing facility 1318 are tasks that require accessing large databases (e.g., restaurant guides) and/or need a more powerful computing device than can be provided by the in-ear utility device 1301a.

Existing computerized applications can be enabled for operation on, or in conjunction with, the in-ear utility device 1301a, according to an embodiment of the invention. Thus, a user may be able to access applications such as Skype translator, Google translator, WeChat, Facebook message, etc. via the in-ear utility device 1301a, according to an embodiment of the invention. In some embodiments, a version of one of these existing applications may be tailored for operation on the in-ear utility device 1301a, e.g., some portion of the application resides on the in-ear utility device 1301a with other application tasks handled remotely. In other embodiments, the in-ear utility device 1301a may simply engage a remote application.

Tasks that may be amenable to processing outside the in-ear utility device include voice authentication, artificial intelligence, speech recognition, and real-time translation. However, each of these tasks can also be performed entirely or partially on the in-ear utility device 1301a. So, for example, the in-ear utility device 1301a may be configured to perform some simple translation tasks while leaving more complicated tasks to processing outside the in-ear utility device. Thus, the processor of the in-ear utility device 1301a may be configured to understand which tasks it can perform itself and which tasks require assistance from another device, according to an embodiment of the invention.

Similarly, the processor (e.g., the processor 207 shown in FIG. 2A) may also be configured for notification response management, according to an embodiment of the invention. So, for example, the in-ear utility device 1301a may be paired with the smartphone 1314. The smartphone 1314 may have calendar and/or alarm functions. The smartphone 1314 may not filter its calendar/alarm messages (e.g., "The butcher turns 50 today."). However, the user of the in-ear utility device 1301a may not want to hear from the speaker of the in-ear utility device 1301a every calendar/alarm message provided by the smartphone 1301a.

The processor on the in-ear utility device 1301a may be configured by the user to play only calendar/alarm messages at or above a particular threshold, according to an embodiment of the invention. The calendar/alarm filter could be provided either on the smartphone 1314 and/or on the in-ear utility device 1301a, according to an embodiment of the invention. The calendar/alarm filter could also be provided by an external utility such as Google Calendar. The filter, could, for example, be an extension to Google Calendar or a similar function.

In operation, for example, the filter instructs the in-ear utility device 1301a to play only high priority alarm messages. Alternatively, the filter may reside on the smartphone 1314 or remote computing facility 1318 and simply determine a subset of alarm messages to send to the in-ear utility device 1301a, and the in-ear utility device 1301a plays all the alarm messages of that subset that it receives. So, for example, "Job interview in 5 minutes" may have the highest priority, and the platform (e.g., the smartphone 1314 and/or the remote computing facility 1318) hosting the calendar/alarm filter may send this message to the in-ear utility device 1301a for playing to the user while the platform decides not to send "Send flowers to Joe sometime today" to the in-ear utility device 1301a such that the user won't hear this message via the in-ear utility device 1301a, according to an embodiment of the invention.

The filtering function itself may be adjustable by the user and/or automatically by particular events, according to an embodiment of the invention. For example, as previously discussed, the in-ear utility device 1301a may include a driver safety application. If the in-ear utility device 1301a (or a related external system) becomes aware that the user is driving an automobile, then the calendar/alarm function may automatically engage (or be engaged by an external system in the automobile itself) to thwart the playing of all calendar/alarm messages and/or such calendar/alarm messages not at or above a high threshold, according to an embodiment of the invention.

In addition, the processor on the in-ear utility device 1301a may also be configured not to play calendar/alarm messages when the in-ear utility device 1301a is aware that the user is speaking, according to an embodiment of the invention. The in-ear utility device 1301a may then schedule replaying of the calendar/alarm message after the passage of a predetermined amount of time, according to an embodiment of the invention. As previously discussed, the microphones on the in-ear utility device 1301a may be configured to listen to the user's acoustic environment.

Similarly, as mentioned above, existing applications (e.g., WeChat) may be enabled for operation on the in-ear utility device 1301a. Once these applications have been enabled, the filtering function described above may also be applied to notifications provided by these applications as well, according to an embodiment of the invention. Thus, the filter in conjunction with the application can determine when, where, and how notifications from these applications are delivered to the user. In other words, not all notifications may be provided to the user through the speaker of the in-ear utility device 1301a residing in the user's ear 1305a, according to an embodiment of the invention.

Various embodiments of the invention have been described in detail with reference to the accompanying drawings. References made to particular examples and implementations are for illustrative purposes, and are not intended to limit the scope of the invention or the claims.

It should be apparent to those skilled in the art that many more modifications of the in-ear utility device besides those already described are possible without departing from the inventive concepts herein. The inventive subject matter, therefore, is not to be restricted except by the scope of the appended claims. Moreover, in interpreting both the specification and the claims, all terms should be interpreted in the broadest possible manner consistent with the context.

Headings and sub-headings provided herein have been provided as an assistance to the reader and are not meant to limit the scope of the invention disclosed herein. Headings and sub-headings are not intended to be the sole or exclusive location for the discussion of a particular topic.

While specific embodiments of the invention have been illustrated and described, it will be clear that the invention is not limited to these embodiments only. Embodiments of the invention discussed herein may have generally implied the use of materials from certain named equipment manufacturers; however, the invention may be adapted for use with equipment from other sources and manufacturers. Equipment used in conjunction with the invention may be configured to operate according to conventional protocols (e.g., Wi-Fi) and/or may be configured to operate according to specialized protocols. Numerous modifications, changes, variations, substitutions and equivalents will be apparent to those skilled in the art without departing from the spirit and scope of the invention as described in the claims. In general, in the following claims, the terms used should not be construed to limit the invention to the specific embodiments disclosed in the specification, but should be construed to include all systems and methods that operate under the claims set forth hereinbelow. Thus, it is intended that the invention covers the modifications and variations of this invention provided they come within the scope of the appended claims and their equivalents.

It should be noted that while many embodiments of the invention described herein are drawn to a smart wireless in-ear utility device, various configurations are deemed suitable and may employ various computing devices including servers, interfaces, systems, databases, agents, engines, controllers, or other types of computing devices operating individually or collectively. One should appreciate that any referenced computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed smart in-ear utility device.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

As used herein, and unless the context dictates otherwise, the terms "ambient noise" and "ambient sound" have been used synonymously. Similarly, "sound" and "noise" have been used synonymously, except where the context shows a difference in meaning, e.g., "meaningful sound from mere noise." Likewise, "coupled to" is intended to include both direct coupling (in which two elements that are coupled to each other contact each other) and indirect coupling (in which at least one additional element is located between the two elements). Therefore, the terms "coupled to" and "coupled with" are used synonymously. The terms "coupled to" and "coupled with" are also used euphemistically to mean "communicatively coupled with" where two or more networked devices are able to send or receive data over a network.

We claim:

1. A communication network, comprising:
   a plurality of in-ear utility devices, each in-ear utility device, comprising:
      a body having at least a portion shaped to fit into a user's ear canal;
      a plurality of sensors in the body that receive data related to the user of the in-ear utility device;
      a processor in the body examines the data received by the plurality of sensors; and
      a transceiver in the body,
   wherein the processor forwards the data received by the plurality of sensors to a computing facility in the communication network via the transceiver; and
   a computing facility having a computer processor, wherein the computer processor in the computer facility exceeds a computing capacity of the processors in each of the in-ear utility device of the plurality of in-ear utility devices, and having a database,
   wherein the computing facility upon receiving the data from the plurality of sensors from an in-ear utility device of the plurality of in-ear utility devices, analyzes the data from the plurality of sensors with respect to the user of the in-ear utility device of the plurality of in-ear utility devices using additional data from the database and analyzes the data received from the plurality of sensors from the in-ear utility device of the plurality of in-ear utility devices with respect to other data stored in the database received from a plurality of sensors associated with other in-ear utility devices of the plurality of in-ear utility devices.

2. The communication network of claim 1 wherein at least one sensor of the plurality of sensors in each in-ear utility device of the plurality of in-ear utility devices is from the group comprising a thermometer, a heart rate monitor, a $VO_2$ Max monitor, a pulse oximetry monitor, a respiratory rate monitor, a respiratory monitor, an oxygen consumption monitor, a cardiac efficiency monitor, a heart rate variability monitor, a metabolic rate monitor, a blood pressure monitor, an EEG data monitor, a galvanic skin response monitor, an EKG/ECG monitor, a blood analyte monitor, an ambient temperature monitor, and a humidity monitor.

3. The communication network of claim 1 wherein each in-ear utility device of the plurality of in-ear utility devices further comprises:
   a data storage component located in the body;
   a speaker located at a proximal end of the body, wherein if the processor determines that data received by a sensor of the plurality of sensors exceeds a predetermined threshold, the processor retrieves from the data storage component an audio warning file and directs playing of the audio warning file through the speaker.

4. The communication network of claim 1, wherein each in-ear utility device of the plurality of in-ear utility devices further comprises:
   a speaker located at a proximal end of the body; and
   a sensor of the plurality of sensors configured to measure a data element, wherein the sensor and the processor are configured to operate as a measurement device that provides one of an alarm, a stop watch, a calendar, and a notification function, wherein if the data element exceeds a predetermined threshold, the processor sends a sound notification to the speaker.

5. The communication network of claim 1, wherein the body of each in-ear utility device of the plurality of in-ear utility devices has a proximal end configured to reside in the user's ear canal at a distance from 8 to 12 millimeters away from the user's ear drum.

6. The communication network of claim 1, wherein the body of each in-ear utility device of the plurality of in-ear utility devices has a first portion and a second portion, the second portion shaped to fit into the user's ear canal, each in-ear utility device of the plurality of in-ear utility devices further comprising:
 a swivel joint connecting the first portion of the body to the second portion of the body, the swivel joint configured to facilitate placement of the in-ear utility device into the user's ear canal; and
 a flexible seal covering at least a portion of the second portion of the body.

7. The communication network of claim 6 wherein the flexible seal is composed of a material having a Shore A Durometer hardness value between 10 and 30.

8. The communication network of claim 1, wherein each in-ear utility device of the plurality of in-ear utility devices further comprises:
 a voice-focused microphone port located on an external surface of the body and configured to receive external sounds into the in-ear utility device, the voice-focused microphone port residing at a fixed distance between the user's mouth and the user's ear canal when the body resides in the user's ear canal, wherein the voice-focused microphone port is located at a position on the external surface of the body to receive the external sounds naturally amplified by a pinna of the user's ear;
 a voice-focused microphone in the body that receives the external sounds via the voice-focused microphone port, wherein the received external sounds include sounds representing the user's voice;
 a data storage component having a voice profile for the user's voice; and
 a voice recognition chip in the body configured to recognize the user's voice using the external sounds received from the voice-focused microphone, the voice recognition chip configured to examine the voice profile and configured to apply the fixed distance between the user's mouth and the ear canal in recognizing the user's voice.

9. The communication network of claim 1, wherein each in-ear utility device of the plurality of in-ear utility devices further comprises:
 a speaker located at the proximal end of the body;
 a microphone located at a distal end of the body and configured to convert sounds external to the in-ear utility device into an electrical signal; and
 an amplifier configured to increase power of the electrical signal,
 wherein the processor has been configured to operate the speaker, the microphone, and the amplifier as a hearing device that receives external sounds in the microphone and converts the external sounds to the electrical signal, amplifies the electrical signal in the amplifier, and delivers the electrical signal to the speaker.

10. The communication network of claim 1, wherein each in-ear utility device of the plurality of in-ear utility devices further comprises:
 an accelerometer located in the body, the accelerometer configured to detect taps on the user's body and record tap data including tap intensity and tap duration, wherein the detected taps represent commands from the in-ear utility device user,
 wherein the processor receives tap data from the accelerometer and determines if the received tap data matches a predetermined pattern for a predetermined action, wherein the processor engages the predetermined action on the in-ear utility device when the received tap data matches the predetermined pattern.

11. A communication network, comprising:
 a plurality of in-ear utility devices, each in-ear utility device, comprising:
 a body having at least a portion shaped to fit into a user's ear canal;
 at least one microphone in the body that receives external sounds to the in-car utility device, including sounds produced by the user of the in-ear utility device;
 a processor in the body configured to examine the external sounds; and
 a transceiver in the body,
 wherein the processor upon detecting a database request in the external sounds received via the microphone from the user of the in-ear utility device forwards the database request to a computing facility in the communication network via the transceiver; and
 a computing facility having a computer processor, wherein the computer processor in the computer facility exceeds a computing capacity of the processors in each of the in-ear utility device of the plurality of in-ear utility devices, and having a database,
 wherein the computing facility upon receiving a database request from an in-ear utility device of the plurality of in-ear utility devices, finds requested data in the database and returns the requested data to the in-ear utility device of the plurality of in-ear utility devices via the transceiver.

12. The communication network of claim 11 wherein at least one sensor of the plurality of sensors in each in-ear utility device of the plurality of in-ear utility devices is from the group comprising a thermometer, a heart rate monitor, a $VO_2$ Max monitor, a pulse oximetry monitor, a respiratory rate monitor, a respiratory monitor, an oxygen consumption monitor, a cardiac efficiency monitor, a heart rate variability monitor, a metabolic rate monitor, a blood pressure monitor, an EEG data monitor, a galvanic skin response monitor, an EKG/ECG monitor, a blood analyte monitor, an ambient temperature monitor, and a humidity monitor.

13. The communication network of claim 11 wherein each in-ear utility device of the plurality of in-ear utility devices further comprises:
 a data storage component located in the body;
 a speaker located at a proximal end of the body, wherein if the processor determines that data received by a sensor of the plurality of sensors exceeds a predetermined threshold, the processor retrieves from the data storage component an audio warning file and directs playing of the audio warning file through the speaker.

14. The communication network of claim 11, wherein each in-ear utility device of the plurality of in-ear utility devices further comprises:
 a speaker located at a proximal end of the body; and
 a sensor of the plurality of sensors configured to measure a data element, wherein the sensor and the processor are configured to operate as a measurement device that provides one of an alarm, a stop watch, a calendar, and a notification function, wherein if the data element exceeds a predetermined threshold, the processor sends a sound notification to the speaker.

15. The communication network of claim 11, wherein the body of each in-ear utility device of the plurality of in-ear utility devices has a proximal end configured to reside in the user's ear canal at a distance from 8 to 12 millimeters away from the user's ear drum.

16. The communication network of claim 11, wherein the body of each in-ear utility device of the plurality of in-ear utility devices has a first portion and a second portion, the second portion shaped to fit into the user's ear canal, each in-ear utility device of the plurality of in-ear utility devices further comprising:
    a swivel joint connecting the first portion of the body to the second portion of the body, the swivel joint configured to facilitate placement of the in-ear utility device into the user's ear canal; and
    a flexible seal covering at least a portion of the second portion of the body.

17. The communication network of claim 16 wherein the flexible seal is composed of a material having a Shore A Durometer hardness value between 10 and 30.

18. The communication network of claim 11, wherein each in-ear utility device of the plurality of in-ear utility devices further comprises:
    a voice-focused microphone port located on an external surface of the body and configured to receive external sounds into the in-ear utility device, the voice-focused microphone port residing at a fixed distance between the user's mouth and the user's ear canal when the body resides in the user's ear canal, wherein the voice-focused microphone port is located at a position on the external surface of the body to receive the external sounds naturally amplified by a pinna of the user's ear;
    a voice-focused microphone in the body that receives the external sounds via the voice-focused microphone port, wherein the received external sounds include sounds representing the user's voice;
    a data storage component having a voice profile for the user's voice; and
    a voice recognition chip in the body configured to recognize the user's voice using the external sounds received from the voice-focused microphone, the voice recognition chip configured to examine the voice profile and configured to apply the fixed distance between the user's mouth and the ear canal in recognizing the user's voice.

19. The communication network of claim 11, wherein each in-ear utility device of the plurality of in-ear utility devices further comprises:
    a speaker located at the proximal end of the body;
    a microphone located at a distal end of the body and configured to convert sounds external to the in-ear utility device into an electrical signal; and
    an amplifier configured to increase power of the electrical signal,
    wherein the processor has been configured to operate the speaker, the microphone, and the amplifier as a hearing device that receives external sounds in the microphone and converts the external sounds to the electrical signal, amplifies the electrical signal in the amplifier, and delivers the electrical signal to the speaker.

20. The communication network of claim 11, wherein each in-ear utility device of the plurality of in-ear utility devices further comprises:
    an accelerometer located in the body, the accelerometer configured to detect taps on the user's body and record tap data including tap intensity and tap duration, wherein the detected taps represent commands from the in-ear utility device user,
    wherein the processor receives tap data from the accelerometer and determines if the received tap data matches a predetermined pattern for a predetermined action, wherein the processor engages the predetermined action on the in-ear utility device when the received tap data matches the predetermined pattern.

* * * * *